(12) United States Patent
Slootstra et al.

(10) Patent No.: US 7,972,993 B2
(45) Date of Patent: Jul. 5, 2011

(54) IDENTIFICATION OF PROTEIN BINDING SITES

(75) Inventors: Jelle Wouter Slootstra, Lelystad (NL); Wouter Cornelis Puijk, Lelystad (NL); Robbert Hans Meloen, Niezyl (NL); Pieter van Dijken, Harderwijk (NL); Evert van Dijk, Giethoorn (NL)

(73) Assignee: Pepscan Systems B.V., Lelystad (NL)

( * ) Notice: Subject to any disclaimer, the term of this patent is extended or adjusted under 35 U.S.C. 154(b) by 255 days.

(21) Appl. No.: 10/411,869

(22) Filed: Apr. 10, 2003

(65) Prior Publication Data

US 2003/0228605 A1 Dec. 11, 2003

Related U.S. Application Data

(63) Continuation of application No. PCT/NL01/00744, filed on Oct. 10, 2001.

(30) Foreign Application Priority Data

Oct. 11, 2000 (EP) ..................................... 00203518

(51) Int. Cl.
*C40B 50/14* (2006.01)
(52) U.S. Cl. .................. 506/30; 506/7; 506/13; 506/23
(58) Field of Classification Search .................... None
See application file for complete search history.

(56) References Cited

U.S. PATENT DOCUMENTS

| | | | |
|---|---|---|---|
| 5,368,712 A | 11/1994 | Tomich et al. | |
| 5,474,895 A * | 12/1995 | Ishii et al. .......................... | 435/6 |
| 5,595,915 A * | 1/1997 | Geysen ......................... | 436/518 |
| 5,770,772 A * | 6/1998 | Aono et al. .................... | 564/218 |
| 5,824,483 A | 10/1998 | Houston, Jr. et al. | |
| 5,830,637 A | 11/1998 | Frank et al. | |
| 5,885,577 A | 3/1999 | Alvarez | |
| 6,015,561 A | 1/2000 | Alvarez | |
| 6,461,812 B2 * | 10/2002 | Barth et al. ....................... | 435/6 |
| 6,642,353 B1 | 11/2003 | McConnell et al. | |

FOREIGN PATENT DOCUMENTS

| | | |
|---|---|---|
| EP | 1 197 755 A1 | 4/2002 |
| JP | 04-204379 | 7/1992 |
| JP | 2000-235036 | 8/2000 |
| WO | WO 84/03564 A1 | 9/1984 |
| WO | WO 93/09872 A1 | 5/1993 |
| WO | WO 98/09411 A1 | 3/1996 |
| WO | WO 97/00267 A1 | 1/1997 |
| WO | WO 00/11223 A1 | 3/2000 |
| WO | WO 02/31510 A1 | 4/2002 |

OTHER PUBLICATIONS

Reineke et al., "Identification of miniproteins using cellulose-bound duotope scans," Peptides for the New Millennium, The 16th Proceedings of the American Peptide Symposium, presented in Minneapolis, MN, United States, Jun. 26-Jul. 1, 1999 (2000), Meeting Date 1999, 167-169; Eds.: Fields et al., Kluwer Academic Publishers, Dordrecht, Netherlands.*
Reineke et al., Nature Biotechnology 17:271-275 (1999).*
Englebretsen et al., Peptide Research 7(6), 322 326 (1994).*
Sila et al., Journal of Molecular Recognition 8:29-34 (1995).*
Writer et al., Immunology vol. 95, No. suppl. 1, pp. 32, Meeting Info.: 6th Annual Congress of the British Society for Immunolgy (1998).*
International Search Report, International Application No. PCT/NL01/00744, dated Feb. 13, 2002 (4 pages).
Reineke, Ulrich, et al., "A synthetic mimic of a discontinuous binding site on interleukin-10," 17(3) Nature Biotechnology 271-275 (Mar. 1999).

* cited by examiner

*Primary Examiner* — Jeffrey S. Lundgren
(74) *Attorney, Agent, or Firm* — TraskBritt, P.C.

(57) ABSTRACT

The invention relates to the field of molecular recognition or detection of discontinuous or conformational binding sites or epitopes corresponding to a binding molecule, in particular, in relation to protein-protein, protein-nucleic acid, nucleic acid-nucleic acid or biomolecule-ligand interactions. The invention provides a synthetic molecular library allowing testing for, identification, characterization or detection of a discontinuous binding site capable of interacting with a binding molecule, the library having been provided with a plurality of test entities, each test entity comprising at least one first segment spotted next to a second segment, each segment having the capacity of being a potential single part of a discontinuous binding site.

12 Claims, 20 Drawing Sheets

Cysteine protection.

| Protecting Group | Cleavage Reagent | Comments |
| --- | --- | --- |
| Acm | $Hg^{2+}$, $I_2$, $Ag^+$, $Tl^{3+}$ | Stable to TFA. Enables peptide to be purified in a protected form prior to liberation of the easily oxidizable thiol groups. Removal of Acm and simultaneous disulphide bond formation can be carried out by treatment with $I_2$ or $Tl^{3+}$. |
| tBu | $Hg^{2+}$, TCIMS/ PhSoOh, TFMSA | Stable to TFA and iodine oxidation. Treatment with $MeSiCl_3$/ PhSOPh removes t-Bu and cyclizes in one step without scrambling existing disulphide bonds. |
| Trt | TFA, $I_2$, $Tl^{3+}$ | Most useful derivative for routine use in Fmoc SPPS as it generates the sulfydryl peptide directly from the TFA cleavage reaction. |
| tButhio | RSH, $R_3P$ | Stable to TFA providing thiol scavengers are not used. Has been used in combination with Acm for selective formation of two disulphide bonds. |
| Mmt | 1% TFA in DCM | Can be selectively removed whilst the peptide remains attaches to the solid phase. Ideal for on-resin disulphide bond formation or modification of Cys side-chain. |
| Npys | RSH, $R_3P$ | Stable to TFA providing thiol scavengers are not used. Activates thiol groups towards disulphide bond formation. Useful for the selective preparation of mixed disulphides. |

Fig. 1

Selection and Improvement of Binding Bodies

Fig. 11

1.  +AVRSSSRTPSDKPVZ
2.  +VRSSSRTPSDKPVAZ
3.  +RSSSRTPSDKPVAHZ
4.  +SSSRTPSDKPVAHVZ
5.  +SSRTPSDKPVAHVVZ

Etc.

145. +FAESGQVYFGIIALZ

Fig. 12

Grid-44

Grid-46

Grid-48

|     | 1   | 2   | 3   | 4   | 5   | 6   | 7   | 8   | 9   | 10  | 11  | 12  |
|-----|-----|-----|-----|-----|-----|-----|-----|-----|-----|-----|-----|-----|
| 13  | 14  | 15  | 16  | 17  | 18  | 19  | 20  | 21  | 22  | 23  | 24  | 25  |
| 26  | 27  | 28  | 29  | 30  | 31  | 32  | 33  | 34  | 35  | 36  | 37  | 38  |
| 39  | 40  | 41  | 42  | 43  | 44  | 45  | 46  | 47  | 48  | 49  | 50  | 51  |
| 52  | 53  | 54  | 55  | 56  | 57  | 58  | 59  | 60  | 61  | 62  | 63  | 64  |
| 65  | 66  | 67  | 68  | 69  | 70  | 71  | 72  | 73  | 74  | 75  | 76  | 77  |
| 78  | 79  | 80  | 81  | 82  | 83  | 84  | 85  | 86  | 87  | 88  | 89  | 90  |
| 91  | 92  | 93  | 94  | 95  | 96  | 97  | 98  | 99  | 100 | 101 | 102 | 103 |
| 104 | 105 | 106 | 107 | 108 | 109 | 110 | 111 | 112 | 113 | 114 | 115 | 116 |
| 117 | 118 | 119 | 120 | 121 | 122 | 123 | 124 | 125 | 126 | 127 | 128 | 129 |
| 130 | 131 | 132 | 133 | 134 | 135 | 136 | 137 | 138 | 139 | 140 | 141 | 142 |
| 143 | 144 | 145 |     |     |     |     |     |     |     |     |     |     |

65
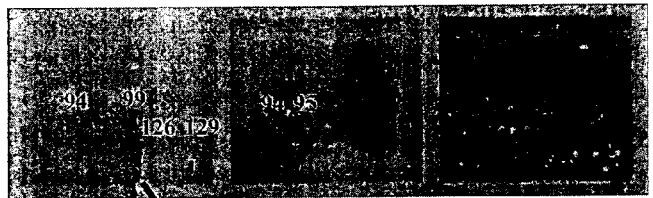
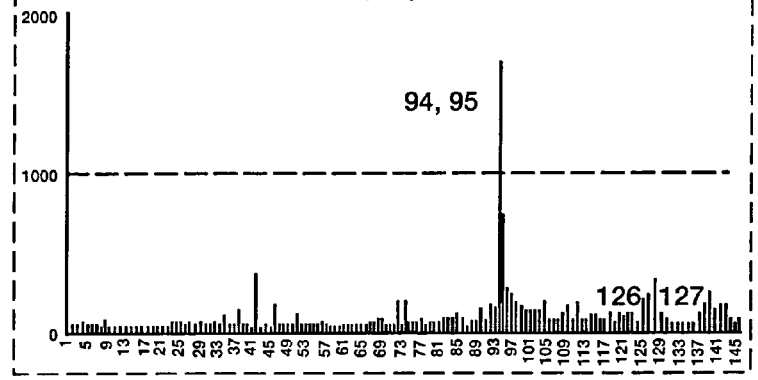
127
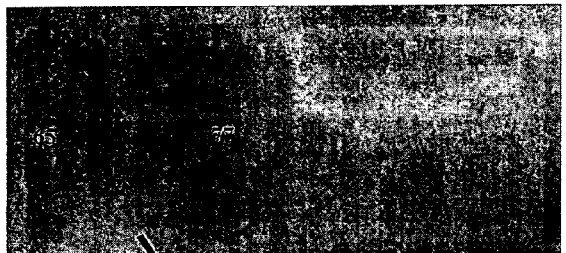
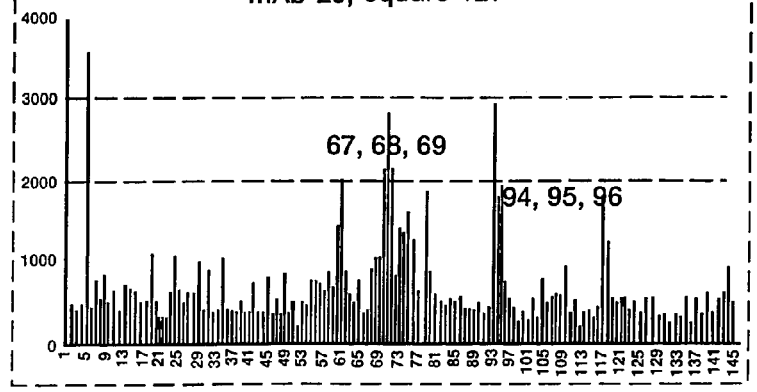
Fig. 14

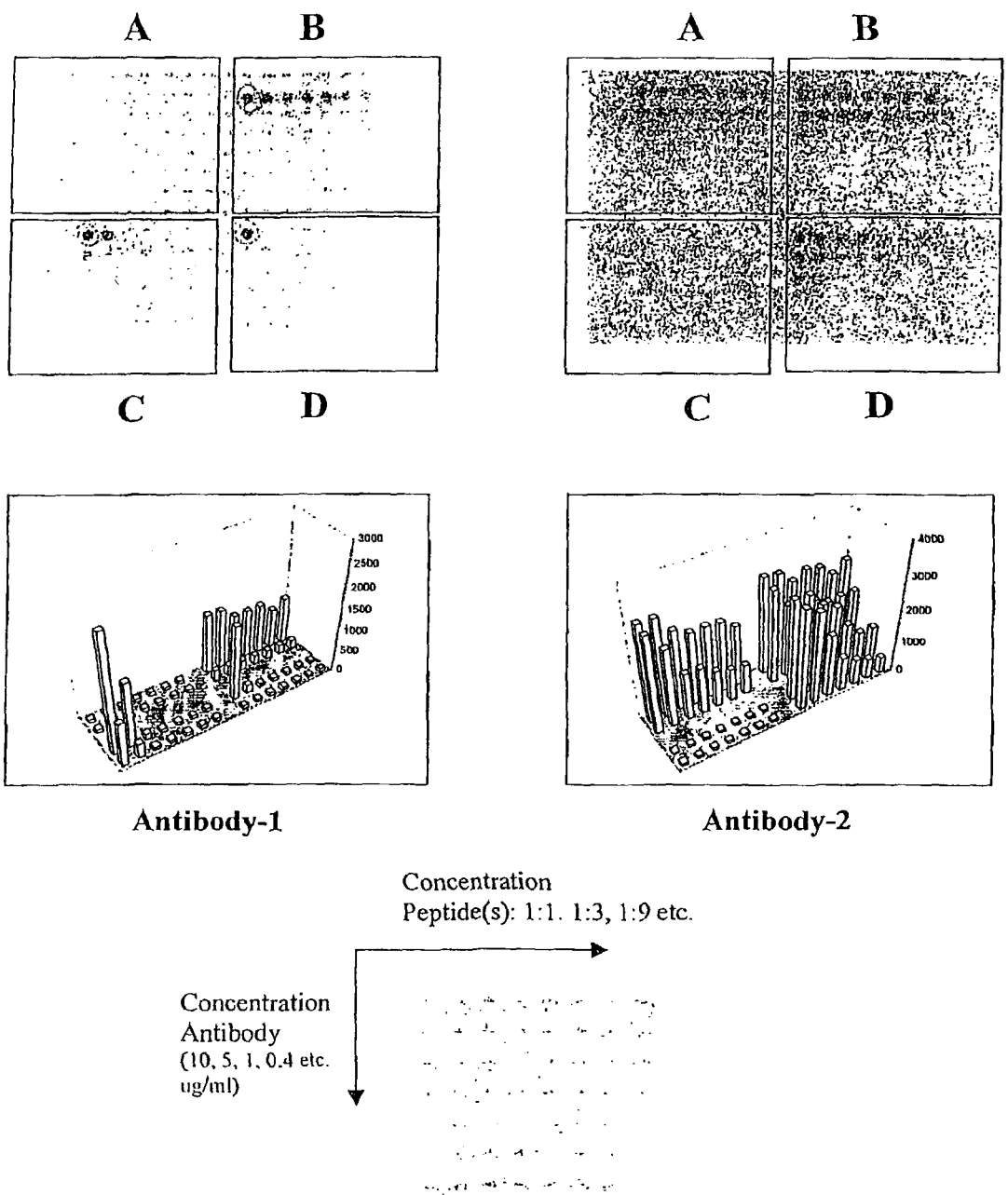

SEQUENCE LISTING

<160> NUMBER OF SEQ ID NOS: 65

<210> SEQ ID NO 1
<211> LENGTH: 40
<212> TYPE: PRT
<213> ORGANISM: Artificial
<220> FEATURE:
<223> OTHER INFORMATION: Synthetic hFSH peptide

<400> SEQUENCE: 1

Glu Lys Glu Glu Ala Arg Phe Cys Ile Ser Ile Asn Thr Thr Trp Ala
1               5                   10                  15

Ala Gly Tyr Ala Tyr Thr Arg Asp Leu Val Tyr Lys Asp Pro Ala Arg
            20                  25                  30

Pro Lys Ile Gln Lys Thr Ala Thr
        35                  40

<210> SEQ ID NO 2
<211> LENGTH: 12
<212> TYPE: PRT
<213> ORGANISM: Artificial
<220> FEATURE:
<223> OTHER INFORMATION: Synthetic 12-mer from linear sequence of hTNF

<400> SEQUENCE: 2

Ile Lys Ser Pro Cys Gln Arg Glu Thr Pro Glu Gly
1               5                   10

<210> SEQ ID NO 3
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 3

Ala Val Arg Ser Ser Ser Arg Thr Pro Ser Asp Lys Pro Val Glx
1               5                   10                  15

<210> SEQ ID NO 4
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 4

Val Arg Ser Ser Ser Arg Thr Pro Ser Asp Lys Pro Val Ala Glx
1               5                   10                  15

<210> SEQ ID NO 5
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 5

Arg Ser Ser Ser Arg Thr Pro Ser Asp Lys Pro Val Ala His Glx
1               5                   10                  15

<210> SEQ ID NO 6

```
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 6

Ser Ser Ser Arg Thr Pro Ser Asp Lys Pro Val Ala His Val Glx
1               5                   10                  15

<210> SEQ ID NO 7
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 7

Ser Ser Arg Thr Pro Ser Asp Lys Pro Val Ala His Val Val Glx
1               5                   10                  15

<210> SEQ ID NO 8
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 8

Phe Ala Glu Ser Gly Gln Val Tyr Phe Gly Ile Ile Ala Leu Glx
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 9

Phe Lys Gly Gln Gly Cys Pro Ser Thr His Val Leu Leu Thr Glx
1               5                   10                  15

<210> SEQ ID NO 10
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 10

Lys Gly Gln Gly Cys Pro Ser Thr His Val Leu Leu Thr His Glx
1               5                   10                  15

<210> SEQ ID NO 11
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 11

Gly Gln Gly Cys Pro Ser Thr His Val Leu Leu Thr His Thr Glx
```

```
1               5                   10                  15
```

<210> SEQ ID NO 12
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 12

```
Ser Tyr Gln Thr Lys Val Asn Leu Leu Ser Ala Ile Lys Ser Glx
1               5                   10                  15
```

<210> SEQ ID NO 13
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 13

```
Tyr Gln Thr Lys Val Asn Leu Leu Ser Ala Ile Lys Ser Pro Glx
1               5                   10                  15
```

```
<400> SEQUENCE: 17

Glu Lys Gly Asp Arg Leu Ser Ala Glu Ile Asn Arg Pro Asp Glx
1               5                   10                  15

<210> SEQ ID NO 18
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 18

Phe Lys Gly Gln Gly Cys Pro Ser Thr His Val Leu Leu Thr Glx
1               5                   10                  15

<210> SEQ ID NO 19
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 19

Cys Pro Ser Thr His Val Leu Leu Thr His Thr Ile Ser Arg Glx
1               5                   10                  15

<210> SEQ ID NO 20
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 20

Ser Thr His Val Leu Leu Thr His Thr Ile Ser Arg Ile Ala Glx
1               5                   10                  15

<210> SEQ ID NO 21
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 21

Leu Thr His Thr Ile Ser Arg Ile Ala Val Ser Tyr Gln Thr Glx
1               5                   10                  15

<210> SEQ ID NO 22
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 22

Leu Leu Ser Ala Ile Lys Ser Pro Cys Gln Arg Glu Thr Pro Glx
1               5                   10                  15

<210> SEQ ID NO 23
<211> LENGTH: 15
<212> TYPE: PRT
```

-continued

```
<213> ORGANISM: Artificial
<220> FEATURE:
<223> OTHER INFORMATION: Synthetic 15-mer loop-peptide from linear
      sequence of hTNF

<400> SEQUENCE: 23

Leu Ser Ala Ile Lys Ser Pro Cys Gln Arg Glu Thr Pro Glu Glx
1               5                   10                  15

<210> SEQ ID NO 24
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 24

Lys Ser Pro Cys Gln Arg Glu Thr Pro Glu Gly Ala Glu Ala Glx
1               5                   10                  15

<210> SEQ ID NO 25
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 25

Gln Leu Glu Lys Gly Asp Arg Leu Ser Ala Glu Ile Asn Arg Glx
1               5                   10                  15

<210> SEQ ID NO 26
<211> LENGTH: 15
<212> TYPE: PRT
<213> ORGANISM: Artificial
<220> FEATURE:
<223> OTHER INFORMATION: Synthetic 15-mer loop-peptide from linear
      sequence of hTNF

<400> SEQUENCE: 26

Lys Gly Asp Arg Leu Ser Ala Glu Ile Asn Arg Pro Asp Tyr Glx
1               5                   10                  15

<210> SEQ ID NO 27
<211> LENGTH: 16
<212> TYPE: PRT
<213> ORGANISM: Human

<400> SEQUENCE: 27

Gly Gln Gly Cys Pro Ser Thr His Val Leu Leu Thr His Thr Ile Ser
1               5                   10                  15

<210> SEQ ID NO 28
<211> LENGTH: 10
<212> TYPE: PRT
<213> ORGANISM: Human

<400> SEQUENCE: 28

Ser Ala Ile Lys Ser Pro Cys Gln Arg Glu
1               5                   10

<210> SEQ ID NO 29
<211> LENGTH: 11
<212> TYPE: PRT
<213> ORGANISM: Human
```

-continued

```
<400> SEQUENCE: 29

Lys Gly Asp Arg Leu Ser Ala Glu Ile Asn Arg
1               5                   10

<210> SEQ ID NO 30
<211> LENGTH: 11
<212> TYPE: PRT
<213> ORGANISM: Artificial
<220> FEATURE:
<223> OTHER INFORMATION: HCDR3 of 1fld.pdb

<400> SEQUENCE: 30

Ala Arg Glu Arg Asp Tyr Arg Leu Asp Tyr Glx
1               5                   10

<210> SEQ ID NO 31
<211> LENGTH: 10
<212> TYPE: PRT
<213> ORGANISM: Artificial
<220> FEATURE:
<223> OTHER INFORMATION: HCDR3 of 1mlb.pdb

<400> SEQUENCE: 31

Ala Arg Gly Asp Gly Asn Tyr Gly Tyr Glx
1               5                   10

<210> SEQ ID NO 32
<211> LENGTH: 10
<212> TYPE: PRT
<213> ORGANISM: Artificial
<220> FEATURE:
<223> OTHER INFORMATION: HCDR3 of 3hfl.pdb

<400> SEQUENCE: 32

Leu His Gly Asn Tyr Asp Phe Asp Gly Glx
1               5                   10

<210> SEQ ID NO 33
<211> LENGTH: 8
<212> TYPE: PRT
<213> ORGANISM: Artificial
<220> FEATURE:
<223> OTHER INFORMATION: HCDR3 of 3hfm.pdb

<400> SEQUENCE: 33

Ala Asn Trp Asp Gly Asp Tyr Glx
1               5

<210> SEQ ID NO 34
<211> LENGTH: 11
<212> TYPE: PRT
<213> ORGANISM: Artificial
<220> FEATURE:
<223> OTHER INFORMATION: HCDR3 of 1qfw.pdb

<400> SEQUENCE: 34

Ala Arg Arg Tyr Gly Asn Ser Phe Asp Tyr Glx
1               5                   10

<210> SEQ ID NO 35
<211> LENGTH: 13
<212> TYPE: PRT
<213> ORGANISM: Artificial
<220> FEATURE:
<223> OTHER INFORMATION: HCDR3 of 1qfw.pdb

<400> SEQUENCE: 35
```

```
Ala Arg Gln Gly Thr Ala Ala Gln Pro Tyr Trp Tyr Glx
1               5                   10
```

<210> SEQ ID NO 36
<211> LENGTH: 12
<212> TYPE: PRT
<213> ORGANISM: Artificial
<220> FEATURE:
<223> OTHER INFORMATION: LCDR1 of 1fdl.pdb

<400> SEQUENCE: 36

```
Arg Ala Ser Gly Asn Ile His Asn Tyr Leu Ala Glx
1               5                   10
```

<210> SEQ ID NO 37
<211> LENGTH: 12
<212> TYPE: PRT
<213> ORGANISM: Artificial
<220> FEATURE:
<223> OTHER INFORMATION: LCDR1 of 1mlb.pdb

<400> SEQUENCE: 37

```
Arg Ala Ser Gln Ser Ile Ser Asn Asn Leu His Glx
1               5                   10
```

<210> SEQ ID NO 38
<211> LENGTH: 11
<212> TYPE: PRT
<213> ORGANISM: Artificial
<220> FEATURE:
<223> OTHER INFORMATION: LCDR1 of 3hfl.pdb

<400> SEQUENCE: 38

```
Ser Ala Ser Ser Ser Val Asn Tyr Met Tyr Glx
1               5                   10
```

<210> SEQ ID NO 39
<211> LENGTH: 12
<212> TYPE: PRT
<213> ORGANISM: Artificial
<220> FEATURE:
<223> OTHER INFORMATION: LCDR1 of 3hfm.pdb

<400> SEQUENCE: 39

```
Arg Ala Ser Gln Ser Ile Gly Asn Asn Leu His Glx
1               5                   10
```

<210> SEQ ID NO 40
<211> LENGTH: 13
<212> TYPE: PRT
<213> ORGANISM: Artificial
<220> FEATURE:
<223> OTHER INFORMATION: LCDR1 of 1qfw.pdb

<400> SEQUENCE: 40

```
Arg Ala Ser Glu Ser Val Asp Ser Tyr Gly Asn Ser Glx
1               5                   10
```

<210> SEQ ID NO 41
<211> LENGTH: 13
<212> TYPE: PRT
<213> ORGANISM: Artificial
<220> FEATURE:
<223> OTHER INFORMATION: LCDR1 of 1qfw.pdb

<400> SEQUENCE: 41

```
Ala Ser Glu Ser Val Asp Ser Tyr Gly Asn Ser Phe Glx
1               5                   10
```

```
<210> SEQ ID NO 42
<211> LENGTH: 13
<212> TYPE: PRT
<213> ORGANISM: Artificial
<220> FEATURE:
<223> OTHER INFORMATION: LCDR1 of 1qfw.pdb

<400> SEQUENCE: 42

Ser Glu Ser Val Asp Ser Tyr Gly Asn Ser Phe Met Glx
1               5                   10

<210> SEQ ID NO 43
<211> LENGTH: 13
<212> TYPE: PRT
<213> ORGANISM: Artificial
<220> FEATURE:
<223> OTHER INFORMATION: LCDR1 of 1qfw.pdb

<400> SEQUENCE: 43

Glu Ser Val Asp Ser Tyr Gly Asn Ser Phe Met Gln Glx
1               5                   10

<210> SEQ ID NO 44
<211> LENGTH: 14
<212> TYPE: PRT
<213> ORGANISM: Artificial
<220> FEATURE:
<223> OTHER INFORMATION: LCDR1 of 1qfw.pdb

<400> SEQUENCE: 44

Arg Ala Ser Glu Ser Val Asp Ser Tyr Gly Asn Ser Phe Glx
1               5                   10

<210> SEQ ID NO 45
<211> LENGTH: 14
<212> TYPE: PRT
<213> ORGANISM: Artificial
<220> FEATURE:
<223> OTHER INFORMATION: LCDR1 of 1qfw.pdb

<400> SEQUENCE: 45

Ala Ser Glu Ser Val Asp Ser Tyr Gly Asn Ser Phe Met Glx
1               5                   10

<210> SEQ ID NO 46
<211> LENGTH: 14
<212> TYPE: PRT
<213> ORGANISM: Artificial
<220> FEATURE:
<223> OTHER INFORMATION: LCDR1 of 1qfw.pdb

<400> SEQUENCE: 46

Ser Glu Ser Val Asp Ser Tyr Gly Asn Ser Phe Met Gln Glx
1               5                   10

<210> SEQ ID NO 47
<211> LENGTH: 15
<212> TYPE: PRT
<213> ORGANISM: Artificial
<220> FEATURE:
<223> OTHER INFORMATION: LCDR1 of 1qfw.pdb

<400> SEQUENCE: 47

Arg Ala Ser Glu Ser Val Asp Ser Tyr Gly Asn Ser Phe Met Glx
1               5                   10                  15
```

```
<210> SEQ ID NO 48
<211> LENGTH: 15
<212> TYPE: PRT
<213> ORGANISM: Artificial
<220> FEATURE:
<223> OTHER INFORMATION: LCDR1 of 1qfw.pdb

<400> SEQUENCE: 48

Ala Ser Glu Ser Val Asp Ser Tyr Gly Asn Ser Phe Met Gln Glx
1               5                   10                  15

<210> SEQ ID NO 49
<211> LENGTH: 16
<212> TYPE: PRT
<213> ORGANISM: Artificial
<220> FEATURE:
<223> OTHER INFORMATION: LCDR1 of 1qfw.pdb

<400> SEQUENCE: 49

Arg Ala Ser Glu Ser Val Asp Ser Tyr Gly Asn Ser Phe Met Gln Glx
1               5                   10                  15

<210> SEQ ID NO 50
<211> LENGTH: 12
<212> TYPE: PRT
<213> ORGANISM: Artificial
<220> FEATURE:
<223> OTHER INFORMATION: LCDR1 of 1qfw.pdb

<400> SEQUENCE: 50

Lys Ala Ser Glu Thr Val Asp Ser Phe Val Ser Glx
1               5                   10

<210> SEQ ID NO 51
<211> LENGTH: 13
<212> TYPE: PRT
<213> ORGANISM: Artificial
<220> FEATURE:
<223> OTHER INFORMATION: LCDR2 of 1fdl.pdb

<400> SEQUENCE: 51

Leu Leu Val Tyr Tyr Thr Thr Thr Leu Ala Asp Gly Glx
1               5                   10

<210> SEQ ID NO 52
<211> LENGTH: 13
<212> TYPE: PRT
<213> ORGANISM: Artificial
<220> FEATURE:
<223> OTHER INFORMATION: LCDR2 of 1mlb.pdb

<400> SEQUENCE: 52

Leu Leu Ile Lys Tyr Val Ser Gln Ser Ser Ser Gly Glx
1               5                   10

<210> SEQ ID NO 53
<211> LENGTH: 13
<212> TYPE: PRT
<213> ORGANISM: Artificial
<220> FEATURE:
<223> OTHER INFORMATION: LCDR2 of 3hfl.pdb

<400> SEQUENCE: 53

Arg Trp Ile Tyr Asp Thr Ser Lys Leu Ala Ser Gly Glx
1               5                   10

<210> SEQ ID NO 54
<211> LENGTH: 13
```

```
<212> TYPE: PRT
<213> ORGANISM: Artificial
<220> FEATURE:
<223> OTHER INFORMATION: LCDR2 of 3hfm.pdb

<400> SEQUENCE: 54

Leu Leu Ile Lys Tyr Ala Ser Gln Ser Ile Ser Gly Glx
1               5                   10

<210> SEQ ID NO 55
<211> LENGTH: 13
<212> TYPE: PRT
<213> ORGANISM: Artificial
<220> FEATURE:
<223> OTHER INFORMATION: LCDR2 of 1qfw.pdb

<400> SEQUENCE: 55

Leu Leu Ile Tyr Arg Ala Ser Asn Leu Glu Ser Gly Glx
1               5                   10

<210> SEQ ID NO 56
<211> LENGTH: 13
<212> TYPE: PRT
<213> ORGANISM: Artificial
<220> FEATURE:
<223> OTHER INFORMATION: LCDR2 of 1qfw.pdb

<400> SEQUENCE: 56

Leu Leu Ile Phe Gly Ala Ser Asn Arg Glu Ser Gly Glx
1               5                   10

<210> SEQ ID NO 57
<211> LENGTH: 10
<212> TYPE: PRT
<213> ORGANISM: Artificial
<220> FEATURE:
<223> OTHER INFORMATION: LCDR3 of 1fdl.pdb

<400> SEQUENCE: 57

Gln His Phe Trp Ser Thr Pro Arg Thr Glx
1               5                   10

<210> SEQ ID NO 58
<211> LENGTH: 10
<212> TYPE: PRT
<213> ORGANISM: Artificial
<220> FEATURE:
<223> OTHER INFORMATION: LCDR3 of 1mlb.pdb

<400> SEQUENCE: 58

Gln Gln Ser Asn Ser Trp Pro Arg Thr Glx
1               5                   10

<210> SEQ ID NO 59
<211> LENGTH: 9
<212> TYPE: PRT
<213> ORGANISM: Artificial
<220> FEATURE:
<223> OTHER INFORMATION: LCDR3 of 3hfl.pdb

<400> SEQUENCE: 59

Gln Gln Trp Gly Arg Asn Pro Thr Glx
1               5

<210> SEQ ID NO 60
<211> LENGTH: 10
<212> TYPE: PRT
<213> ORGANISM: Artificial
```

```
<220> FEATURE:
<223> OTHER INFORMATION: LCDR3 of 3hfm.pdb

<400> SEQUENCE: 60

Gln Gln Ser Asn Ser Trp Pro Tyr Thr Glx
1               5                   10

<210> SEQ ID NO 61
<211> LENGTH: 12
<212> TYPE: PRT
<213> ORGANISM: Artificial
<220> FEATURE:
<223> OTHER INFORMATION: LCDR3 of 1qfw.pdb

<400> SEQUENCE: 61

Gln Gln Ser Asp Glu Tyr Pro Tyr Met Tyr Thr Glx
1               5                   10

<210> SEQ ID NO 62
<211> LENGTH: 10
<212> TYPE: PRT
<213> ORGANISM: Artificial
<220> FEATURE:
<223> OTHER INFORMATION: LCDR3 of 1qfw.pdb

<400> SEQUENCE: 62

Gly Gln Thr Tyr Asn His Pro Tyr Thr Glx
1               5                   10

<210> SEQ ID NO 63
<211> LENGTH: 16
<212> TYPE: PRT
<213> ORGANISM: Human

<400> SEQUENCE: 63

Lys Ser Tyr Asn Arg Val Thr Val Met Gly Gly Phe Lys Val Glu Glx
1               5                   10                  15

<210> SEQ ID NO 64
<211> LENGTH: 16
<212> TYPE: PRT
<213> ORGANISM: Human

<400> SEQUENCE: 64

Leu Gln Glu Asn Pro Phe Phe Ser Gln Pro Gly Ala Pro Ile Leu Glx
1               5                   10                  15

<210> SEQ ID NO 65
<211> LENGTH: 12
<212> TYPE: PRT
<213> ORGANISM: Human

<400> SEQUENCE: 65

Gly Gln Gly Cys Pro Ser Thr His Val Leu Leu Thr
1               5                   10
```

IDENTIFICATION OF PROTEIN BINDING SITES

CROSS REFERENCE TO RELATED APPLICATIONS

This application is a continuation of International Application PCT/NL01/00744, filed Oct. 10, 2001, designating the United States, published in English Apr. 18, 2002, as WO 02/31510 A1, the contents of which are incorporated herein by this reference.

FIELD OF THE INVENTION

The present invention relates to the field of molecular recognition or detection of discontinuous or conformational binding sites or epitopes corresponding to or interacting with a binding molecule, in particular, in relation to protein-protein or protein-ligand interactions.

BACKGROUND OF THE INVENTION

Interactions between binding molecules, which in general are biomolecules and their corresponding ligands, are central to life. Cells often bear or contain receptor molecules that interact or bind with a hormone, a peptide, a drug, an antigen, an effector molecule or with another receptor molecule; enzymes bind with their substrate; antibody molecules bind with an antigen, nucleic acid with protein, and so on. By "interact or bind" it is meant that the binding molecule and ligand approach each other within the range of molecular forces and may influence each other's properties. This approach takes the binding molecule and its ligand through various stages of molecular recognition comprising increasing degrees of intimacy and mutual effect: they bind.

Binding molecules have this binding ability because they comprise distinct binding sites allowing for the recognition of the ligand in question. The ligand, in turn, has a corresponding binding site, and only when the two binding sites can interact by—essentially spatial—complementarity, the two molecules can bind. Needless to say, molecules having three dimensions have binding sites that are of a three dimensional nature, often one or more surface projections or protuberances of one binding site correspond to one or more pockets or depressions in the other, a three-dimensional lock-and-key arrangement, sometimes in an induced-fit variety.

Sometimes, such a protuberance comprises a single loop of the molecule in question, and it is only this protuberance that essentially forms the binding site. In that case, one often terms these binding sites as comprising a linear or continuous binding site, wherein a mere linear part of the molecule in question is essentially responsible for the binding interaction. This terminology is widely used to describe, for example, antibody-antigen reactions wherein the antigen comprises part of a protein sequence, a linear peptide. One then often speaks about a linear or continuous epitope, wherein the binding site (epitope) of the antigenic molecule is formed by a loop of consecutively bound amino acids. However, similar continuous binding sites (the terms "epitope" and "binding site" are used interchangeably herein) can be found with receptor-antigen interactions (such as with a T-cell receptor), with receptor-ligand interactions such as with hormone receptors and agonists or antagonists thereof, with receptor-cytokine interactions, or with, for example, enzyme-substrate or receptor-drug interactions, whereby a linear part of the molecule is recognized as the binding site, and so on.

More often, however, such a protuberance or protuberances and depressions comprise various, distinct parts of the molecule in question, and the combined parts essentially form the binding site. Commonly, one names such a binding site comprising distinct parts of the molecule in question a discontinuous or conformational binding site or epitope. For example, binding sites laying on proteins having not only a primary structure (the amino acid sequence of the protein molecule), but also secondary and tertiary structure (the folding of the molecule into alpha-helices or beta-sheets and its overall shape), and sometimes even quaternary structure (the interaction with other protein molecules) may comprise in their essential protuberances or depressions amino acids or short peptide sequences that lay far apart in the primary structure but are folded closely together in the binding site.

Due to the central role binding molecules and their ligands play in life, there is an ever expanding interest in testing for or identification of the nature or characteristics of the binding site. Notably, the rapid developments in evolving biotechnology fields such as proteomics will result in the near future in the identification of more and more binding molecules and their corresponding ligands. The detection of protein-protein interactions and enzyme-substrate interactions (not only of protein enzymes but certainly also of for example catalytic RNA-based interactions), and the identification of protein-nucleic acid and of nucleic acid-nucleic acid pairs of binding molecule and corresponding ligand, will certainly result in generating more interest in where the exact interacting (binding) sites between these molecules lay and how one can develop compounds (agonists, antagonists, drugs) modulating the specific interaction.

Not only is one interested in the exact nature of the particular interaction between binding molecule and ligand in question, for example, in order to replace or supplement binding molecules or ligands when needed, but one is also interested in knowing approximating characteristics of the interaction in order to find or design analogues, agonists, antagonists or other compounds mimicking a binding site or ligand involved.

Versatile and rapid methods to test for or identify continuous epitopes or binding sites are known. Most, if not all, nucleic acid detection techniques, and molecular libraries using these, entail hybridization of an essentially continuous nucleic acid stretch with a complementary nucleic acid strand, be it DNA, RNA or PNA. Little attention has been paid to methods allowing rapid and straightforward identification of discontinuous binding sites of an essentially nucleic acid nature. Although plenty of such sites exist, think only of the lack of understanding surrounding ribosomal binding sites where ribosomal proteins bind to tRNA, of regulatory sites in promoter sequences, of interactions between polymerases and replicases between DNA and RNA, of catalytic RNA reactions, and so on, no molecular libraries exist that provide easy access to such sites.

An early work in the peptide field is disclosed in PCT International Publication No. WO 84/03564, related to a method of detecting or determining antigenically active amino acid sequences or peptides in a protein. This work, providing the so-called Pepscan technology, whereby a plurality of different peptides is synthesized by linking with a peptide bond a first amino acid to a second, and so on, and on a second position in the test format yet another first amino acid is linked to a second, and so on, after which the synthesized peptides are each tested with the binding molecule in question, allows the determination of every continuous antigenic determinant or continuous epitope of importance in a protein or peptide sequence. Pepscan technology taken in a broad sense also provides for the testing for or identification of (albeit linear) peptides essentially identical with, analogous to or mimicking binding sites or ligands of a various nature (mimotopes, Geyssen et al., Mol. Immunol. 23:709-715, 1986).

Pepscan technology allows identification of linear peptide sequences interacting with receptor molecules, enzymes, antibodies, and so on, in a rapid and straightforward fashion, allowing testing of a great many peptides for their reactivity with the binding molecule in question with relatively little effort. The order of magnitude of testing capability having been developed with Pepscan technology (e.g., also due to miniaturization of test formats; see, e.g., PCT International Publication No. WO 93/09872) furthermore allows at-random testing of a multiplicity of peptides, leading to automated combinatorial chemistry formats wherein a great many binding molecules are tested in a (if so desired at-random) pattern for their reactivity with a molecular library of synthetic peptides representing potential continuous binding sites or ligands, allowing the rapid detection of particularly relevant molecules out of tens of thousands of combinations of molecules tested.

However, for the testing of discontinuous or conformational binding sites to a binding molecule, no formats similar to or as versatile as Pepscan technology exist. Attempts to identify discontinuous epitopes by Pepscan technology are cumbersome. It does, in general, not suffice to merely extend synthesis of the test peptides by linking more amino acids to the existing peptide and hoping that some of the thus formed longer peptides will fold in such a way that at least two distinct parts are presented in a discontinuous fashion and are recognized by a binding molecule. In that case, there is no way of finding out in a rapid and straightforward fashion that the binding is indeed through a discontinuous binding site; it might be that just a longer single loop is responsible for the binding.

Some additional possibilities are provided by testing synthetic peptide sequences that have been designed to comprise two previously identified parts of a binding site, each part in essence being linear and being part of a larger linear peptide. Early work herein was done by Atassi and Zablocki (J. Biol. Chem 252:8784, 1977) who describe that spatially or conformationally contiguous surface residues (which are otherwise distant in sequence) of an antigenic site of egg white lysozyme were linked by peptide bonds into a single peptide which does not exist in lysozyme but attempts to simulate a surface region of it. However, their technique, called surface simulation synthesis, requires detailed knowledge of the three-dimensional structure of the protein under study and a full chemical identification of the residues constituting the binding site beforehand, as well as their accurate conformational spacing and directional requirements.

In the same fashion, Dimarchi et al. (Science 232:339-641, 1986) describe a 38 to 40 amino acid-long synthetic peptide consisting of two previously identified separate peptidyl regions of a virus coat protein. The peptide was synthesized using common peptide synthesis technology (Merrifield et al., Biochemistry 21, 5020, 1982) by adding subsequent amino acids with a peptide bond to an ever growing peptide resulting in a peptide wherein the two peptidyl regions were connected by a diproline spacer presumably functioning as indication of a secondary structural turn, thereby providing a two-part epitope or binding site.

However, it is clear that when one has to know beforehand the sequence of the (in this case only) two relevant parts in order to provide the desired discontinuous binding site, it excludes the feasibility of providing (desirably in a random fashion) a whole array of merely potential discontinuous binding sites for large scale testing. Furthermore, a major drawback of the above-mentioned strategies is that, again, only linear epitopes or dominant binding regions of discontinuous epitopes can be mimicked adequately. For the more complete synthesis of a discontinuous binding site, all the contributing parts have to be arranged in the proper conformation to achieve high-affinity binding. Therefore, single parts of discontinuous binding sites have to be linked.

Fifteen years after Dimarchi, Reineke et al. (Nature Biotechnology, 17:271-275, 1999) provided a synthetic mimic of a discontinuous binding site on a cytokine and a method to find such a discontinuous binding site that allowed for some flexibility and somewhat larger scale testing, wherein positionally addressable peptide collections derived from two separate regions of the cytokine were displayed on continuous cellulose membranes and substituted in the process to find the best binding peptide. After selection of the "best reactors" from each region, these were combined to give rise to another synthetic peptide collection (comprising peptides named duotopes) that again underwent several rounds of substitutions.

Reineke et al. thus provide synthesis of peptide chains comprising duotopes, however, again selected after previous identification of putative constituting parts with Pepscan technology, thereby still not allowing testing discontinuous binding sites in a rapid and straight forward fashion.

However, as indicated before, protein domains or small molecules that mimic binding sites are playing an increasing role in drug discovery, diagnostics and biotechnology. The search for particular molecules that bind to a binding site and mimic or antagonize the action of a natural ligand has been initiated in many laboratories. As indicated before, attempts to find such structures in synthetic molecular libraries often fail because of the essentially discontinuous nature and spatial complementarity of most binding sites.

Thus, for the many more cases where the binding site may essentially be discontinuous, improved means and methods to identify these sites are needed, and, in particular, means and methods are needed that allow testing for discontinuous binding sites whereby said parts need not necessarily first be selected by previous identification as a putative or even only tentative constituting part of the desired discontinuous binding site but bear only the potentiality of being part of that site by being a molecule with more or less distinct features per se.

BRIEF SUMMARY OF THE INVENTION

The invention provides a method for producing a molecular library comprising providing the library with a plurality of test entities wherein said entities have essentially been produced by segment spotting, that is, by spotting, placing, or attaching in close proximity at least two (di-, tri-, oligo- or multimeric) segments of, for example, nucleic acids or peptides directly or indirectly to a solid phase, such as an array surface, instead of by sequentially synthesizing test molecules and spotting one molecule, or several replicas of said one molecule, as a single entity, which is done traditionally. In theory, the segments can be sequentially synthesized in close proximity to each other, whereby in a repetitive fashion one monomer (e.g., a nucleotide or an amino acid) to another until a (in essence polymeric) molecule (segment) of the desired length has been obtained.

Essentially, existing nucleic acid libraries comprise nucleic acids that are synthesized sequentially by adding one nucleotide or nucleoside at a time to the growing stretch, and existing peptide libraries comprise peptides that are synthesized sequentially by adding one amino acid at the time to a growing stretch until the desired length has been reached. However, with existing libraries, no attention is given to synthesizing specific segments in close proximity to each other so that they together can represent a putative binding site. With nucleic acids, the monomers are essentially selected from a limited set of well known nucleotides. With peptides, the monomers are essentially selected from a well known set of amino acids. Not only naturally occurring monomers are used. Synthetic nucleotides, such as peptide nucleic acid (PNA) molecules, non-naturally occurring amino acids, or even D-amino acids, are routinely used as monomers by which the essentially polymeric molecules are generated or produced using a method that is essentially in conformity with the sequential synthesis of polymers from monomeric molecules in nature. Preferred, according to the invention, however, is synthesizing the segments before they are attached to the solid phase in close proximity, thereby it is easier to create the desired test entity, the putative binding site composed of two or more segments located in close proximity and attached to the solid phase, e.g., the array surface.

In close proximity herein reflects the possibility that a putative binding molecule can bind to at least two of the closely spotted segments or parts thereof and is defined in angstrom units, reflecting the generally molecular scale of the binding sites. It is preferred to attach the two or more segments that form the desired test entity at no more than 100 angstroms away from each other, however, obviating the need of long linkers, or when small segments are used, distances of smaller than 50, or preferably smaller than 30, or even smaller than 15 angstroms, are preferred, the smaller distances in general creating a better fit for binding sites. Minimal proximity is 1-2 angstroms, whereby the segments are, for example, linked to variously protected thiol groups only 1-2 atoms on the polymer away from each other. Furthermore, the length of a flexible linker should preferably be 10-100 angstroms, where the preferred length of segments is at about 5-100 angstroms and where the preferred distance between the tops of segments amounts to 0-30 angstroms.

For example, two segments can be coupled, preferably as loops, onto a (polycarbon)-polymer surface. With extra spaced building blocks (for example, phenylalanine amino acids) it is provided to obtain extended loops. On the (polycarbon)-surface, for example, two types (see FIG. 1 for suitable types) of protected cysteines (e.g., cys (trt) and cys (mmt)) and, for example, one spacing building block is coupled. The cys (mmt) is deprotected with 1% TFA while the cys (trt) remains protected. The first segment is coupled to the deprotected cys (mmt). Then, the second cys (trt) is deprotected with 95% TFA. Then, the second segment is coupled to the now deprotected cys (trt). If desired, segments can also be linked together using appropriate chemistry.

Alternatively, instead of directly linking the segments to the surface (albeit via linkage groups), the segments may be first linked to a template that itself is linked to the surface. In a preferred embodiment, such a template is, for example, a peptide. For example, two segments can be coupled onto a cyclic template that itself is coupled to the polymer surface. The cyclic template is, for example, a cyclic flexible peptide. The cyclic peptide contains, for example, reactive groups such as four lysines (mmt), two cysteines (trt) and two cysteines (butyl). The template is, for example coupled to the resin via a sulphur.

The invention thus provides a molecular library that, albeit also suited for detecting or screening for continuous binding sites, is now particularly well suited for detecting or screening for discontinuous binding sites, in particular in relation to binding molecule-ligand interactions such as, for example, protein-protein, protein-nucleic acid, and nucleic acid-nucleic acid interactions, now that at least two different segments, each of which may represent a part of a discontinuous binding site, are spotted as single entity, tentatively representing a possibly as yet unknown discontinuous binding site, herein also called a binding body.

As used herein, the term "binding body" is generally used for essentially all-peptide segment constructs, however, the technology, as described for all-peptide combinations, can of course also be used for nucleic acid combinations or combinations of an even more mixed nature. A binding body, which is in essence a synthetic molecule comprising a binding site identifiable or obtainable by a method according to the invention as described herein, is essentially a combination of random peptide segments (fixed into one molecule or represented as one molecule on a test s which acts as a binding molecule such as an antibody. Just as in the case of antibodies, the recognition may more or less be "degenerate," i.e., the binding site on the target molecule need not always be optimal. The binding body may in principle bind to any part of the target molecule. For instance: to neutralize the action of TNF-alfa, one might develop a small molecule that specifically interacts with the receptor binding site on TNF-alfa; alternatively, one might develop an antibody that interacts with TNF-alfa at an as yet undefined place and neutralizes its action. This shows that sometimes small molecules are the solution and sometimes large antibodies. Unfortunately, both have their disadvantages: small molecules are difficult or impossible to make for large recognition sites, and large molecules like antibodies are much easier to develop but cannot be used intracellularly and have all sorts of pharmacological disadvantages like their immunogenicity and their inability to act inside the cell.

The advantageous properties of the binding body combine those of small and large molecules: binding bodies share advantages of both. A preferred binding body consists of random peptide segments, for example, slightly biased or shuffled to resemble CDRs or other binding domains. If needed or desired, CDRs may be mimicked by using, for example, 6 segments, each representing one possible CDR, however, combinations of 2, 3 or 4 segments will already provide diversity. The peptide segments preferably are linked at both sides to a scaffold or solid phase. Thus, binding bodies are made up of molecules with one, two or more peptide segments.

Highly diverse binding body libraries can be generated based on systematic combination of relatively small numbers of random peptide segments. A library of 100 binding bodies is easily produced using positionally defined peptide segment arrays as described herein. Screening of such a library with any given molecule is simple, fast and straightforward. Hits can be translated directly into the amino acid or segment make up of the binding body due to the positionally defined array. A library of 10,000 binding bodies can be easily generated by combining all peptides from smaller libraries with each other or by starting with a larger solid support surface. A library of 1,000,000 binding bodies can, for example, be easily generated by combining all peptides of smaller libraries into binding bodies that contain three segments. Thus, a large diversity of binding bodies can be generated starting with relatively small numbers of random peptides (for instance, 10) and multiple combinations of peptides combined into a single binding body (for instance, 6) to arrive at a diversity of 1,000,000 or even larger.

Alternatively, the same binding body diversity can be obtained starting with, for example, 1000 random peptides and using just two peptide segments for each binding body. Just like antibodies, binding bodies can "mature." Based on hits obtained with an initial set of random binding bodies (above), new dedicated libraries can be generated that will contain a high number of improved combinations. The best ones can be selected or improved in an additional round using a second dedicated library, and so on. Development of high affinity binding bodies is thus provided by chemistry to bind peptides, preferably both ends, to a molecular scaffold or solid phase by using an array system in which each binding body is positionally defined, further by appropriate miniaturization and/or by appropriate bioinformatics to analyze the data and to design subsequent improved binding bodies or dedicated libraries of binding bodies.

The two or more different segments can, of course, each be selected at random from any set of di-, tri-, or oligomeric sequences, such as from di-, tri,- or oligonucleotides, or di-, tri-, or oligopeptides, but sometimes, it may be preferred to include at least one specific segment in the entity, specific in the sense that it has been selected from among known segments or distinct parts of biomolecules, such as parts of genes, proteins, enzymes, nucleic acids or unique fragments thereof, proteins involved in up- or down-regulation of translation, t-RNAs, SNRPs, antibodies, complementarity determining regions (CDRs), antigens, receptors, transport proteins, transcription factors or factors involved in up- or down-regulation of transcription, promoter sequences such as, but not necessarily restricted to, the well known TATA-box elements, repressor sites, operator sites and other control elements, polymerases, and replicases, in short, from among known segments or distinct parts of binding molecules known or suspected to be involved in binding via a discontinuous binding site.

Known segments or parts thereof spotted in close proximity may, of course, be already known as parts constituting a discontinuous binding site. However, previous identification as such is essentially not necessary, since screening for such sites with a molecular library according to the invention allows rapid and straightforward identification of the constituting segments or parts thereof.

Screening such a library can easily be envisioned when the library's molecules differ only in that constituting segments are chosen in an overlapping fashion, whereby a first segment from a distinct biomolecule is spotted next to a second, and to a third, and to a fourth segment, and a second is spotted next to a third, and to a fourth, and so on, if so required, until all possible segments of the biomolecule have been spotted in close proximity two-by-two (or three-by-three, or even more) together, which allows for a systematic screening of possible discontinuous binding sites present on the biomolecule.

However, an overlapping fashion is, of course, not required. Random segment combinations spotted in close proximity will provide valuable information about binding sites as well.

The invention thus provides a method for producing a molecular library for identification or detection of a binding site capable of interacting with a binding molecule, and, thus, for the identification of a molecule as a binding molecule, the method comprising providing the library with a plurality of segments derived from binding molecules or their ligands, further comprising spotting at least two of the segments in a pair, or three in a threesome, or more in the respective plurality, preferably a greater part of the pairs, threesomes on pluralities, most preferably essentially all of the pairs, threesomes or pluralities, by at least spotting a first segment next to a second segment, for example, a segment which comprises a dimer, trimer, oligomer or multimer.

Existing libraries, be they of, for example, nucleic acid (containing a repetitive back-bone of nucleotides, nucleosides or peptide nucleic acid, or combinations of these) or amino acid (containing a repetitive back-bone of amino acids) nature have in general in common that single molecules (or single segments) or a plurality of replicas of the single molecules are spotted and used as the entity representing the binding site. Such libraries comprise oligomeric or multimeric molecules, such as stretches of nucleic acids or amino acids, that have been produced by sequentially linking, in a repetitive fashion, one monomer (e.g., a nucleotide or an amino acid) to another, until a (in essence polymeric) molecule of the desired length has been obtained.

Essentially, existing nucleic acid libraries comprise nucleic acids that are synthesized sequentially by adding one nucleotide or nucleoside at a time to the growing stretch, and existing peptide libraries comprise peptides that are synthesized sequentially by adding one amino acid at the time to a growing stretch, until the desired length has been reached. With nucleic acids, the monomers are essentially selected from a limited set of well known nucleotides. With peptides, the monomers are essentially selected from a well known set of amino acids. Not only naturally occurring monomers are used. Synthetic nucleotides, such as peptide nucleic acid (PNA) molecules, non-naturally occurring amino acids, or even D-amino acids, are routinely used as monomers by which the essentially polymeric molecules are generated or produced using a method that is essentially in conformity with the sequential synthesis of polymers from monomeric molecules in nature. These single monomers are then spotted in a single fashion, one monomer thought to represent the full, or nearly the full, binding site, without taking into consideration the multiple parts of a binding site constituting a discontinuous binding site.

The invention provides the recognition that essentially using dimeric or even larger (tri-, oligo-, or multimeric) segments in combination, thus in pairs or threesomes or even more, offers distinct advantages. It not only provides a faster method to arrive at or recognize a molecule composed of various segments, it also provides for fast and efficient shuffling of segments to generate a molecule or test entity repertoire for the desired library. The invention for example provides a method wherein synthesis is started with a monomer in close proximity to which a second segment comprising a dimer, such as a dinucleotide or a dipeptide, is spotted. Herein, a segment comprising a dimer at least consists of a dimer but can also be, for example, a trimer or any-other multimer linking monomers of any nature, as required. Of course, once two segments have been spotted in close proximity, further segments can be added thereto.

In a preferred embodiment, to speed up further synthesis, or to be able to select distinct desired segments, the invention provides a method wherein the first segment also comprises a dimer, and in a yet even more preferred method, further segments comprise dimers as well. In a preferred embodiment, the dimer comprises a dinucleotide or dipeptide, but of course other dimers can be made also. The invention is further explained in the detailed description where several of the examples relate to libraries comprising molecules wherein each of the segments comprises a peptide, such as a tri-, a penta-, an octa-, or nonapeptide. It is, however, also provided by the invention to use longer segments, e.g., 10 to 15, 15 to 20, 20 to 30 or 30 to 40 amino acids or nucleic acids long or longer and to use of a varied nature, e.g. wherein one comprises a nucleic acid and another comprises a peptide, to better mimic binding sites that are found, for example, on nucleic acid-protein complexes.

In a preferred embodiment, as, for example, shown in the examples, the invention provides a method wherein the first segment is spotted or attached to the solid phase by a thioether bond next to the second segment; however, the invention is, of course, not limited thereto. Nucleotide/side segments can, for example, be covalently linked or ligated by splicing enzymes or ligases or by overlapping a first segment and the second segment with an in essence relatively short nucleotide strand that is partly complementary to both segments.

The invention thus provides a molecular library allowing testing for, identification, characterization or detection of a continuous or discontinuous binding site capable of interacting with a binding molecule, the library having been provided with pluralities (pairs, threesomes, foursomes, fivesomes, sixsomes) of segments, each plurality preferably comprising at least one first segment spotted in close proximity to a second segment, wherein at least the second segment previously existed as a dimer or a multimer. Preferably, each segment or part thereof having the capacity to be a potential single part of a discontinuous binding site, preferably wherein each of at least a first and a second segment or part thereof represents a potential single part of a discontinuous binding site. Such a library can, for example, comprise a synthetic molecular library made by chemical spotting of segments.

Preferably, such segments have distinct features, for example, by being in essence segments that are, comprise or mimic molecular components of living organisms, such as (combinations of) nucleotides, sugars, lipids, amino acids, nucleic acid molecules (DNA or RNA), peptide nucleic acid molecules (PNA), carbohydrates, fatty acids or fats.

Herewith, the invention provides synthesis of molecules comprising, separate segments potentially representing at least two distinct parts of a discontinuous binding site, the parts not necessarily first being selected after previous identification of potential constituting parts, thereby allowing testing for discontinuous binding sites in a rapid and straightforward fashion.

The invention thus now allows identifying discontinuous binding sites of receptor molecules that interact or bind at a contact site with a hormone, a peptide, a drug, an antigen, an effector molecule or with another receptor molecule, of enzymes that bind with their substrate, of antibody molecules that bind with a binding site on an antigen, nucleic acid that binds with protein, and so on. In a preferred embodiment of the invention, at least one of the segments comprises a peptide, another segment being, for example, DNA, RNA, PNA, carbohydrate, a fatty acid, a peptide, a hormone or an organic molecule altogether. In one embodiment of the invention, all segments comprise a peptide. In this way, a plurality of different binding bodies is synthesized by spotting a first segment next to a second, and so on, and on a second position in the test or library format yet another first segment is linked to a second, and so on, after which the synthesized binding bodies are each tested with the binding molecule in question, allowing the determination of a discontinuous antigenic determinant or discontinuous epitope of importance in, for example, a nucleic acid, a protein or peptide sequence.

The peptide segment comprises at least two amino acids and can, in principle, be as long as desired, e.g., containing a hundred amino acids or even more. In preferred practice, the peptide segment comprises from 3 to 30, preferably from 4 to 20, even more preferably from 5 or 6 to 12 to 15 amino acids, such as 9 or 12 amino acids. Separate segments, of course, do not necessarily have to be of equal length.

Furthermore, peptide segments to be spotted together, or at least in close proximity to each other, can be selected at random, or under guidance of (a) known protein or peptide sequence(s). Selection at random provides a random library according to the invention. Selection from known protein or peptide sequences is, for example, useful when it is desired to find out whether a discontinuous binding site is composed of distinct sites or parts present at distinct proteins or peptides, for example, in a protein complex to which a particular binding molecule can bind. Selection of various peptide segments from one known protein or peptide sequence is useful when it is desired to find out whether a discontinuous binding site is composed of distinct sites or parts present at one protein or peptide, for example, at a folded protein to which a particular binding molecule can bind. Selection of peptide segments can be done by selecting overlapping peptides from such a known sequence. Overlapping peptides can have, for example, all but one or two amino acids in common, preferably overlapping in a contiguous fashion, or can overlap with only one or several amino acids. For a quick scan for discontinuous binding sites on a known protein, it is, for example, useful to select non-apeptide segments from the protein sequence, of which one has, for example, a 5-amino acid-long overlap with another peptide segment. Equally useful, however, is to select tripeptide segments from the sequence having an overlap of only one amino acid and to use three, or even more, segments in constructing the putative binding site molecule to which the to-be-tested binding molecule can bind.

Of course, such selection strategies are equally applicable to segments of a different nature, nucleic acid segments comprising a certain number of nucleotides, such as 5, 7, 9, and so on, can be selected from known nucleic acid sequences comprising putative or sought-after discontinuous binding sites, each segment selected from a certain position in the known nucleic acid sequence, if desired also in an overlapping fashion. The nucleic acid segment comprises at least 2 nucleotides (be it DNA, RNA or PNA, or functional equivalents thereof), and can, in principle, be as long as desired, e.g., containing a hundred nucleotides or even more. In preferred practice, the nucleic segment comprises from 3 to 30, preferably from 4 to 20, even more preferably from 5 or 6 to 12 to 15 nucleotides, such as 9 or 12 nucleotides. Separate segments, of course, do not necessarily have to be of equal length, and, as the before, can even be of a different nature, e.g., peptide with DNA.

The segments can, for example, be chemically attached to the solid phase by chemical links or bonds. The links or bonds can be formed using many combinations of strategies of, for example, peptide or nucleotide chemistry and selective ligation reactions, as known in the art. Ligation chemistry has been published, for instance, by groups of Kent (Ph. E. Dawson et al., "Synthesis of Proteins by Native Chemical Ligation," Science 266 (1994) 776-779), Tam (J. P. Tam et al., "Peptide Synthesis using Unprotected Peptides through Orthogonal Coupling Methods," Proc. Natl. Acad. Sci. USA 92 (1995) 12485-12489); C. F. Liu et al., ("Orthogonal Ligation of Unprotected Peptide Segments through Pseudoproline Formation for the Synthesis of HIV-1 Protease Analogs," J. Am. Chem. Soc. 118 (1996) 307-312); L. Zhang & J. P. Tam, ("Thiazolidone Formation as a General and Site-specific Conjugation Method for Synthetic Peptides and Proteins," Analytical Biochemistry 233 (1996) 87-93), and Mutter (G. Tuchscherer & M. Mutter, "Protein Design as a Challenge for Peptide Chemists," J. Peptide Science 1 (1995) 3-10); S. E. Cervigni et al., ("Template-assisted Protein Design: Chimeric TASP by Chemoselective Ligation, Peptides: Chemistry, Structure and Biology," P. T. P Kaumaya & R. S. Hodges eds, Mayflower (1996) 555-557).

Possible strategies for the formation of links as preferably provided by the invention are, for example:

1. The link of a segment or segments with a solid phase is formed using a homo- or hetero-bifunctional linking agent (S. S. Wong: Chemistry of Protein Conjugation and Cross-Linking, CRC Press Inc, Boca Raton, Fla. USA 1991). In this construction, a reactive group in a segment is used to react with one part of the bifunctional linking agent, thus facilitating the second part of the linking agent to react with a reactive group from a solid phase, or visa versa. For instance, a linker like MBS (m-maleinimidobenzoic acid N-hydroxysuccinimide ester) can be used to react via its active ester (succinimide) with an amino group of one segment and via its maleinimide group with a free thiol group from a solid phase, or visa versa. In this strategy, when linking preferably no other free amino or thiol groups should be present in the segment. In order to accomplish this, the amino or thiol groups that should be involved in the reaction can be deprotected selectively, for instance, by using a side chain protecting group that can be cleaved by a mild reagent like 1% trifluoroacetic acid, which leaves other side chain protecting groups intact.

2. The link is formed by introduction of a modified amino acid in the synthesis of one or more segments. Amino acids can be modified, for instance, by introduction of a special group at the side-chain or at the alpha-amino group. A modification at the alpha-amino group leads to an amide or backbone modified peptide (see, e.g., Gillon et al., Biopolymers, 31:745-750, 1991). For instance, this group can be a maleinimido group at the side chain amino group of lysine. At the end of the peptide synthesis, this group will react fast and selective with a thiol group of a solid phase. Tam et al. (PNAS 92:12485-12489, 1995) described a synthesis of a peptide with a lysine residue that was modified in the side chain with a protected serine residue. After deprotection and selective oxidation using periodate, the alpha-amino, beta-hydroxy function of the serine is converted into an aldehyde function that can be ligated selectively with another thiol-bearing surface. Also, peptide backbone links, via groups attached to the amide groups of the peptide, can be used to spot segments (Bitan et al., J. Chem. Soc. Perkin Trans.1:1501-1510, 1997; Bitan and Gilon, Tetrahedon, 51:10513-10522, 1995; Kaljuste and Unden, Int. J. Pept. Prot. Res. 43:505-511, 1994).

3. Yet another way to form the link is to synthesize a segment, such as a peptide, with a modified N-terminus. For instance, an N-terminal alpha-haloacetamido group can be introduced at the end of the synthesis. This group reacts fast and selectively with a solid phase which contains a thiol group. For instance, the first segment is synthesized with an N-terminal bromoacetamide and the solid phase is provided with a cysteine. Although most alpha-haloacetamide groups, like chloro-, bromo-, or iodoacetamide, will react with thiol groups, in those cases where speedy assembling is required, the bromoacetamide group is preferred because of its ease of introduction and fast and selective reaction with thiol groups.

Furthermore, the invention provides the possibility to address the link in every position of the first and/or the second or consecutive segment. For instance, for peptide segments, sets of peptides are synthesized in which a cysteine or a side-chain modified lysine (both amino acid residues, in a preferred embodiment, being able to ligate selectively with another segment) shifts from the N-terminal amino acid position one by one to the C-terminal amino acid position. Combinations of these possibilities will, again, lead to libraries as provided by the invention.

In another preferred embodiment, the segments are linked at least twice in close proximity to the solid phase, preferably by linking the respective ends of the segments to the surface, so that, so-to-speak, looped segments are attached to the solid phase. In such a preferred embodiment, pairs (or larger pluralities) of looped segments are attached to the solid phase, presenting themselves as binding bodies.

In a preferred embodiment, the invention provides a library wherein the pluralities are positionally or spatially addressable, e.g., in an array fashion, if desired aided by computer directed localization and/or recognition of a specific pair or threesome (or larger plurality) or set of pluralities within the dimensions (e.g., plane or surface) of the support or solid phase of the library used. In an array, the pluralities are, for example, addressable by their positions in a grid or matrix.

A preferred embodiment of the invention further allows upscaling of the synthesis concerning the number of constructs on, for example, a solid support per square centimeter. To facilitate generation of a great many possible constructs, containing, for example, test entities (pairs, threesomes or larger pluralities) comprising at least two peptide segments of a protein, many thousands of peptide constructs are made. For instance, when all constructs in which both segments are, for instance, twelve amino acids long are derived from a small protein with a length of 100 amino acid residues are needed, already 89×89=7,921 peptide constructs are made if the segments are only linked to the solid phase, for instance, via the C-terminus for the first segment and the N-terminus of the second segment, or visa versa, or both, using only one type of link. For a protein with a length of 1,000 amino acid residues, at least 989×989=978,121 constructs are made. For efficient ELISA testing of these numbers of constructs, high construct densities on the solid support are preferred. High densities of constructs on a solid support are provided by the invention, wherein, for instance, (a layer of) a first segment with a bromoacetamide group at the N-terminus is synthesized on a surface of, for instance, 1 cm$^2$. On yet another part of the surface, another first-segment may be applied. On each of such a peptide-functionalized surface of the support, a set of, for instance, 10, preferably 50, preferably 100, or more second, peptide segments containing a free thiol group are spotted or gridded in a positionally or spatially addressable way, giving, after coupling, so many different peptide pairs. Spotting can, for instance, be done using piezo drop-on-demand technology, or by using miniature solenoid valves. Gridding can, for instance, be done using a set of individual needles that pick up sub-microliter amounts of segment solution from a microtiter plate containing solutions comprising the second segments. After the linking reaction, subsequent deprotection and extensive washing of the support to remove uncoupled peptide gives at least a peptide construct pair density as large as 10 to 50, or even 100 to 200, or up to 50 to 1000 spotted pairs per square centimeter. This density allows the screening of a great many possible peptide pairs or binding bodies derived from the proteins for binding with an antibody. For example: in a preferred embodiment 20,000 to 100,000 constructs are made on 1000 cm$^2$. Typically, the surface is then screened for binding in ELISA with 100 ml of antibody s 1-10 μg of antibody/ml. For example, indirect or direct fluorescence detection allocates antibody binding constructs. Direct fluorescence detection with confocal scanning detection methods, for example, allows antibody detection on spots generated with droplets of peptide-solution in the sub-nano-liter range, making even higher construct densities feasible. Of course, nucleic acid libraries can be made in a similar fashion.

Furthermore, the invention provides a solid support comprising a library according to the invention, the solid support allowing presentation of a potential discontinuous or conformational binding site or epitope to a binding molecule, the solid support having been provided with a plurality of test entities, each pair or threesome or larger plurality of the test entities or binding bodies being a possible representative of the binding site or epitope and, for example, comprising at least one first peptide or nucleotide, for example, covalently linked to a solid phase and a second peptide or nucleotide.

In a preferred embodiment, the solid support comprises at least a spot or dot (e.g., putative binding site, test entity, or pair of segments) density as large as 10, 20, or 50, or even 100, 200, or up to 500 or even 1,000 spots per $cm^2$, preferably wherein the spots or dots are positionally or spatially addressable.

The invention further provides a method to screen for, i.e., test, identify, characterize or detect a discontinuous binding site capable of interacting with a binding molecule, comprising screening a library as provided by the invention with binding molecules, such as there are, for instance, antibodies, soluble receptors, which contain a Fc-tail or a tag for detection, receptors on cells, biotinylated molecules or fluorescent molecules.

Alternative segments could comprise, for instance, carbohydrates, non-natural amino acids, PNAs, DNAs, lipids, or molecules containing peptide bond mimetics. In particular, the invention provides a method to screen for a discontinuous binding site capable of interacting with a binding molecule, comprising screening a library according to the invention with at least one test entity and detecting binding between a member of the library and the test entity. In a preferred embodiment, the binding is detected immunologically, for example, by ELISA techniques.

By detecting binding to a specific test entity (herein also called a binding body) of the library, the invention provides the member or binding body a synthetic molecule comprising the binding body or test entity or pair or larger plurality of (looped) segments comprising a discontinuous binding site identifiable or identified or obtainable or obtained by a method according to the invention. Thus, the invention provides use of a library according to the invention, use of a solid support or solid phase or array surface provided with one or more binding bodies or test entities according to the invention, or use of a method according to the invention for identifying or obtaining a synthetic molecule comprising a discontinuous binding site or a binding molecule capable of binding therewith. Because discontinuous binding sites are now provided, such a synthetic molecule can advantageously be used in vitro or in vivo for finding a binding molecule and for effecting and/or affecting binding to a binding molecule, for example, to interact or bind with receptor molecules that normally interact or bind with a hormone, a peptide, a drug, an antigen, with an effector molecule, with an agonist, with an antagonist, or with another receptor molecule, with enzymes that normally bind with their substrate, with antibody molecules, with nucleic acid, with protein—in short—with biomolecules. The invention is further explained in the detailed description without limiting the invention.

BRIEF DESCRIPTION OF THE SEVERAL VIEWS OF THE DRAWINGS

FIG. 1: six different cysteines that can be used in coupling of bromine under different conditions.

FIG. 11: Partial listing of peptides synthesized for loop-loop 15-mer Matrix-scan (1. +AVRSSSRTPSDKPVZ (SEQ ID NO: 3); 2. +VRSSSRTPSDKPVAZ (SEQ ID NO: 4); 3. +RSSSRTPSDKPVAHZ (SEQ ID NO: 5); 4. +SSSRTPSD-KPVAHVZ (SEQ ID NO: 6); 5. +SSRTPSDKPVAHVVZ (SEQ ID NO: 7); 145. +FAESGQVYFGIIALZ (SEQ ID NO: 8)). All overlapping 15-mer loop-peptides covering the linear sequence of human tumor necrosis factor (hTNF) were synthesized, i.e., 145 hTNF loop-peptides in total. Z is a Cys-butyl. The amino terminus of all peptides contain a bromo-group (+).

FIG. 12: Configuration of the loop-loop 15-mer Matrix-scan. Schematic representation of matrix-scan with two loop segments. On the polymer surface, a mixture of cys (mmt) and cys (trt) are coupled. After 1% TFA, the cys (mmt) is deprotected. Then, in each square, one peptide is coupled via its N-terminal Bromo-group (+). Thus, peptide-1 in square -1, peptide-2 in square-2, etc., until peptide-145 in square-145. Then, the cys(trt) is deprotected with 95% TFA. Then, in each square, 145 different peptides are spotted simultaneously. Thus, peptide-1 to 145 in square-1, peptide 1-145 in square-2, etc., to peptide-1 to peptide-145 in square-145. Some extra squares were used for controls (linear epitopes).

FIG. 14: Result of the loop-loop 15-mer Matrix-scan with mAb 210 (10 ug/m) with details of squares 65 and 127. Combination of loop-peptide 65 with loop-peptides 94, 95, combinations of loop-peptide 65 with 126-127, combinations of loop-peptide 127 with loop-peptides 65-77 and combinations of loop-peptide 127 with loop-peptides 94-96 are labeled. The y-axis is in arbitrary units.

Figure 2:
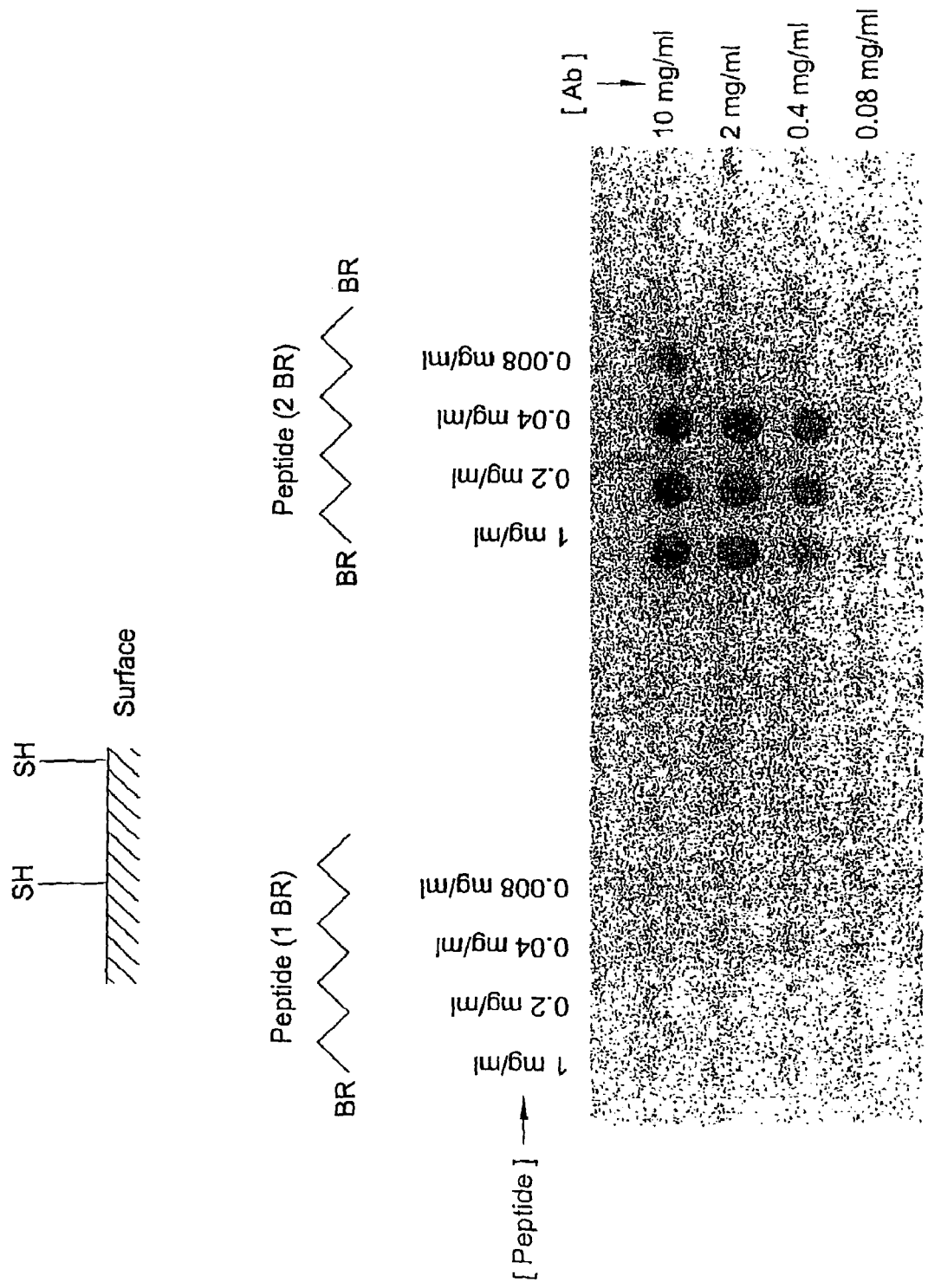
FIG. 2: (spotting with dark coloring) Analysis of two different peptides for showing the advantageous effect of two-sided linking and the formation of loops. On the left, the peptide has an amino-terminal Br. On the right the peptide has an amino-terminal Br and a C-terminal Lysine-Br (synthesized as described in legend FIG. 4B). Test was carried out in a miniwell setup (3 ul each well). Surface is functionalized with thiol groups (—SH groups). Peptides were coupled to the surface using the bromine- (Br—) group of the peptide. Different concentrations of peptide were used for coupling to the surface. Two sets of peptides were used, one with one Br-group and the other (differs only from the previous peptide by an extra lysine+Br-acetyl moiety on the C-terminal site of the peptide) with two Br-groups. Binding was determined using differed antibody concentrations in an ELISA setup.

+ARERDYRLDYZ (SEQ ID NO: 30) (HCDR3 of 1fdl.pdb); Peptide-B: +ARGDGNYGYZ (SEQ ID NO: 31) (HCDR3 of 1mlb.pdb); Peptide-C: +LHGNYDFDGZ (SEQ ID NO: 32) (HCDR3 of 3hfl.pdb); Peptide-D: +ANWDGDYZ (SEQ ID NO: 33) (HCDR3 of 3hfm.pdb); Peptide-E: +ARRYGNSFDYZ (SEQ ID NO: 34) (HCDR3 of 1qfw.pdb); Peptide-F: +ARQGTAAQPYWYZ (SEQ ID NO: 35) (HCDR3 of 1qfw.pdb) (1 fdl.pdb, 1 mlb.pdb, 3hfl.pdb and 3hfm.pdb are antibodies that bind lysozyme; 1 qfw.pdb are two antibodies that bind human choriogonadotrophin). All peptides have an amioterminal bromo-group (+) and a carboxyterminal lysine-mmt (Z).

Peptides 1 to 27:Peptide-1:+RASGNIHNYLAZ (SEQ ID NO: 36) (LCDR1 of 1fdl.pdb); Peptide-2:+RASQSISNNLHZ (SEQ ID NO: 37) (LCDR1 of 1mlb.pdb); Peptide-3:+SASSSVNYMYZ (SEQ ID NO: 38) (LCDR1 of 3hfl.pdb); Peptide-4:+RASQSIGNNLHZ (SEQ ID NO: 39) (LCDR1 of 3hfm.pdb); Peptide-5:+RASESVDSYGNSZ (SEQ ID NO: 40) (LCDR1 of 1qfw.pdb); Peptide-6:+ASESVDSYGNSFZ (SEQ ID NO: 41) (LCDR1 of 1qfw.pdb); Peptide-71:+SESVDSYGNSFMZ (SEQ ID NO: 42) (LCDR1 of 1qfw.pdb); Peptide-8:+ESVDSYGNSFMQZ (SEQ ID NO: 43) (LCDR1 of 1qfw.pdb); Peptide-9:+RASESVDSYGNSFZ (SEQ ID NO: 44) (LCDR1 of 1qfw.pdb); Peptide-10:+ASESVDSYGNSFMZ (SEQ ID NO: 45) (LCDR1 of 1qfw.pdb); Peptide-11:+SESVDSYGNSFMQZ (SEQ ID NO: 46) (LCDR1 of 1qfw.pdb); Peptide-12:+RASESVDSYGNSFMZ (SEQ ID NO: 47) (LCDR1 of 1qfw.pdb); Peptide-13:+ASESVDSYGNSFMQZ (SEQ ID NO: 48) (LCDR1 of 1qfw.pdb); Peptide-14:+RASESVDSYGNSFMQZ (SEQ ID NO: 49) (LCDR1 of 1qfw.pdb); Peptide-15:+KASETVDSFVSZ (SEQ ID NO: 50) (LCDR1 of 1qfw.pdb); Peptide-16:+LLVYYTTTLADGZ (SEQ ID NO: 51) (LCDR2 of 1fdl.pdb); Peptide-17:+LLIKYVSQSSSGZ (SEQ ID NO: 52) (LCDR2 of 1mlb.pdb); Peptide-18:+RWIYDTSKLASGZ (SEQ ID NO: 53) (LCDR2 of 3hfl.pdb); Peptide-19:+LLIKYASQSISGZ (SEQ ID NO: 54) (LCDR2 of 3hfm.pdb); Peptide-20:+LLIYRASNLESGZ (SEQ ID NO: 55) (LCDR2 of 1qfw.pdb); Peptide-21:LLIFGASNRESGZ (SEQ ID NO: 56) (LCDR2 of 1qfw.pdb); Peptide-22:+QHFWSTPRTZ (SEQ ID NO: 57) (LCDR3 of 1fdl.pdb); Peptide-23:+QQSNSWPRTZ (SEQ ID NO: 58) (LCDR3 of 1mlb.pdb); Peptide-24:+QQWGRNPTZ (SEQ ID NO: 59) (LCDR3 of 3hfl.pdb); Peptide-25:+QQSNSWPYTZ (SEQ ID NO: 60) (LCDR3 of 3hfm.pdb); Peptide-26:+QQSDEYPYMYTZ (SEQ ID NO: 61) (LCDR3 of 1qfw.pdb); Peptide-27:+GQTYNHPYTZ (SEQ ID NO: 62) (LCDR3 of 1qfw.pdb) (1 fdl.pdb, 1 mlb.pdb, 3hfl.pdb and 3hfm.pdb are antibodies that bind lysozyme; 1 qfw.pdb are two antibodies that bind human choriogonadotrophin). All peptides have an amioterminal bromo-group (+) and a carboxyterminal lysine-mmt (Z).

The loop-loop peptide pair, +LHGNYDFDGZ (SEQ ID NO: 32) +SESVDSYGNSFMQZ (SEQ ID NO: 46) (loop of HCDR3 of 3hfl.pdb with loop of LCDR1 of 1qfw.pdb) that has the highest binding activity is indicated by arrow.

FIG. 17: Result of Pepscan ELISA with two different antibodies on single or double peptide loops coupled to Pepscan minicards, as described above. Coupled to square-A: Loop peptide-1; Coupled to square-B: first Loop peptide-1 followed by Loop peptide-2; Coupled to square-C: Loop peptide-2; Coupled to square-D: first Loop peptide-2 followed by Loop peptide-1. Loop peptide-1:+KSYNRVTVMGGFKVEZ-conh2 (SEQ ID NO: 63) Loop peptide-2:+LQENPFFSQPGAPILZ-conh2 (SEQ ID NO: 64). The y-axis are optical density values (OD) obtained using a ccd-camera system. Both loop-peptides are derived from human Follicle-Stimulating Hormone (hFSH).

DETAILED DESCRIPTION OF THE INVENTION

Synthesis of Peptide Constructs

A polypropylene or polyethylene support, or of other suitable material, was grafted with, for instance, polyacrylic acid. As an example: a polypropylene support in a 6% acrylic acid solution in water containing $CuSO_4$ was irradiated using gamma radiation at a dose of 12 kGy. The grafted solid support containing carboxylic acid groups was functionalized with amino groups via coupling of t-butyloxycarbonyl-hexamethylenediamine (Boc-HMDA) using dicyclohexylcarbodiimide (DCC) with N-hydroxybenzotriazole (HOBt) and subsequent cleavage of the Boc groups using trifluoroacetic acid. Subsequently, the surface is functionalized with (when preferred, a mixture of differently protected) Cys amino acids using standard Fmoc chemistry. Examples of differently protected Cys groups are Cys (Trt) and Cys (mmt). After removal of the FMOC, the amino group is acetylated. Side chain deprotection can be done as described. Standard Fmoc peptide synthesis chemistry was used to link peptides (segments) on to the amino functionalized solid support. After cleavage of the Fmoc group of the last amino acid and washing, bromoacetic acid was coupled using DCC or DCC/HOBt. A second bromoacetic acid (in the same step) can be coupled to the surface when, for example, a lysine (Lys) residue is present in the peptide: The side chain protection chemistry of Lys (using FMOC-Lys(MTT)-OH) allows that only the amino group of the Lys-side chain is liberated (with 1% trifluoracetic acid in dichloromethane), while the other amino acids still stay protected. Subsequently, if only DCC was used, the peptide did contain a thiol reactive bromoacetamide group. However, if DCC/HOBt was used to couple bromoacetic acid, the peptide essentially did not contain the bromo group, but another reactive group capable of reacting efficiently with thiol groups, thus forming the same thioether link between the segments. Coupling/ligation of a second peptide next to a peptide coupled or synthesized on a solid support: Bromo functionalized peptides can be coupled to the solid support (when a thiol is present) in an aqueous solution containing a sodium bicarbonate buffer at about ph 7-8. Peptides were synthesized at polyethylene pins grafted with poly-hydromethylmethacrylate (poly-HEMA). This graft polymer was made by gamma irradiation of polyethylene pins in a 20% HEMA solution in methanol/water 80/20 or 70/30 at a dose of 30-50 kGy. The functionalized support can be used for the synthesis of 1 μmol of peptide/cm$^2$ after coupling of β-alanine and an acid labile Fmoc-2,4-dimethoxy-4'-(carboxymethyloxy)-benzhydrylamine (Rink) linker. The peptides were synthesized using standard Fmoc chemistry, and the peptide was deprotected and cleaved from the resin using trifluoroacetic acid with scavengers. The cleaved peptide containing a cysteine residue at a concentration of about 1 mg/ml was reacted with the solid support described above in a water/sodium bicarbonate buffer at about pH 7-8, thus forming a partially protected construct of two peptides each at least once covalently bound via a thioether bond to the solid support. The construct described above was deprotected following standard procedures using trifluoroacetic acid/scavenger combinations. The deprotected constructs on the solid support were extensively washed using disrupting buffers containing sodium dodecylsulphate and β-mercaptoethanol and ultrasonic cleaning and were used directly in ELISA. Subsequent cleaning in the disrupt buffers allows repeated testing against antibodies in ELISA.

According to these methods, a library of constructs, for example, consisting of a dodecapeptide segment coupled via its C-terminally added cysteine residue next to a N-terminally bromoacetylated second segment, allowing scanning a protein sequence, for example, by steps of a single amino acid residue. The bromoacetamide peptide was covalently bound to a functionalized polypropylene/polyacrylic acid solid support in 3 µl wells, as described above. The cysteine-containing sequences are synthesized on and cleaved from functionalized polyethylene pins, as described above. Peptides are synthesized on a surface of a solid support, as described above. On this peptide functionalized support, a second peptide segment containing a free thiol group was spotted using piezo drop-on-demand technology using a microdosing apparatus and piezo autopipette (Auto Drop-Micropipette AD-K-501) (Microdrop Gesellschaft fur Mikrodosier Systeme GmbH). Alternatively, spotting or gridding was done using miniature solenoid valves (INKX 0502600A; the Ice Company) or hardened precision ground gridding pins (Genomic Solutions, diameters 0.4, 0.6, 0.8 or 1.5 mm). Subsequent deprotection of the construct and extensive washing to remove uncoupled peptide gave binding body constructs at the spotted area. Peptide constructs generated with peptide solution droplets in the nanoliter-range bind enough antibody for detection, in this case using indirect fluorescence detection. Spots generated with 0.25 nl-50 nl are smaller than 1 mm. Thus, in this set-up, binding body density can be as large as 100-1000 spots per square centimeter. When using smaller equipment, densities can even be higher.

In short, a thiol fuction is introduced on an amino-functionalized solid support. This can be made by a direct reaction of the amino groups with, for instance, iminothiolane or by coupling of Fmoc-Cys(Trt)-OH, followed by Fmoc cleavage using piperidine, acetylation, and trityl deprotection using TFA/scavenger mixtures. This thiol-functionalized solid support can be reacted with, for instance, a bromoacetamide-peptide containing a protected cysteine residue. After coupling of the first peptide, the cysteine can be deprotected using, for instance, a TFA/scavenger mixture. As yet unused free thiol groups can be used to couple a second bromoacetamide-peptide, again containing a protected cysteine. This procedure can be repeated to make segment constructs. Several types of scans can be used in combination with this multi-segment scan.

EXAMPLES OF USE

Proteins and peptides can be screened using any type of binding molecule, e.g., biomolecules such as antibodies, soluble receptors (which contain a Fc-tail or a tag for detection), biotinylated molecules or fluorescent molecules. Alternative segments could be, for instance, carbohydrates, non-natural amino acids, PNAs, DNAs, lipids, and molecules containing peptide bond mimetics.

TSH Example

The design and synthesis of synthetic mimics of discontinuous binding sites of large proteins such as TSH or TSHR is currently desired. Toward this aim, template based mimics of proteins have provided a powerful new tool for basic research. Technology provided herein enables one to map discontinuous binding sites, couple these onto a synthetic template and monitor in detail the structural and functional characteristics.

Pivotal to this approach is the possibility of synthesizing and testing of 100,000s of synthetic peptides in array-format. This is possible with the technologies provided herein. These include peptide-array synthesis and new methodology in template chemistry. Through chemistry, all kinds of synthetic groups are coupled on two or more different positions on these templates, allowing reconstruction of the discontinuous binding sites and the synthesis of mimics. The development of methods that allow mapping of discontinuous binding sites between large proteins is a major research target. Various strategies have been adopted with moderate success. The most successful techniques to date include X-ray crystallography, Combinatorial libraries and Mass-Spectrometry.

We provide a new approach involving peptide-arrays. Peptide array technology has long been used to identify short linear peptides involved in binding. All overlapping linear peptides (12-15-mers) of a given protein are synthesized on a solid-support such as plastic or paper and incubated with the target protein, most often an antibody. Those peptides that are recognized are so-called linear epitopes. Discontinuous epitopes could not be detected. Nevertheless, the early peptide-array technology laid the foundation for methods that identify discontinuous epitopes in a systematic fashion. This made it possible to couple on an array surface any part of a protein (for instance, a peptide of 15 amino acids long) next to any other part of a protein (for instance, a peptide of 15 amino acids long) in any orientation. These arrays, with all possible combinations of peptides, showed in our hands to allow accurate definition of discontinuous epitopes (FIG. 2).

We now focus on discontinuous epitopes involved in Graves disease and Hashimoto disease, but others are as well within reach. The thyroid diseases are autoimmune diseases against the thyroid. The antibodies bind discontinuous epitopes on the thyrotropin receptor on the thyroid gland. Overactivation (Graves) or blockage (Hashimoto) of the thyroid gland leads to serious health problems. Mapping of both the antibody binding regions as well as the TSH binding region greatly contributes to the understanding of both diseases. Subsequently, hTSH and hTSHR mimics of these discontinuous epitopes will be used in new diagnostic tools allowing early discovery of Graves and Hashimoto disease. Studies on human Follicle-Stimulating Hormone (hFSH) and its receptor (hFSHR) have revealed discontinuous binding sites. Biotinylated 40-mers covering various regions of hFSH were tested in a peptide-array binding-assay as herein provided on all overlapping 30-mers covering the linear sequence of hFSHR.

One of the 40-mers clearly bound to a receptor region (FIG. 1). Based on these results a similar study on the hTSH/hSHR couple hTSHR, a hormone-receptor couple that is structurally very similar to the hFSH/hFSHR couple, provides peptides that can be used as diagnostic tools for Graves and/or Hashimoto disease. Patients with Graves or Hashimoto disease develop antibodies against their own thyroid receptors which leads to hyper- or hypothyroidism, respectively. Although the population of antithyrotropin receptor antibodies is heterogeneous, most Graves antibodies bind the N-terminus of the receptor, whereas most Hashimoto antibodies bind the C-terminus of the receptor. In our study, panels of Graves and Hashimoto sera are tested a) for binding in a peptide-array to the set of overlapping 30-mers covering the hTSH-receptor; b) in a competition-assay in which the binding of biotinylated 40-mer TSH-peptides to hTSH-receptor is competed with Graves and Hashimoto sera. In this way, discontinuous binding sites are mapped.

After mapping the discontinuous binding sites, synthetic mimics are designed and synthesized. A primary strategy for synthesis of this kind of synthetic mimics is the synthesis of templates onto which the discontinuous epitope can be reconstructed. The use of templates facilitates the possibility to add various parts of the discontinuous epitope. In this way, hardly any specific binding information will be lost by a high flexibility of the peptide constructs. Attachment of peptides to template structures will closely mimic the native discontinuous epitopes. Recently, much progress has been made in this field. By using stable templates as a framework on which to couple recognition fragments, peptides can be obtained with desired activity.

Further Examples

Examples of Use:

Mapping Discontinuous Epitope on Human Tumor Necrosis Factor (hTNF) (FIGS. 10-15).

Figure 3:
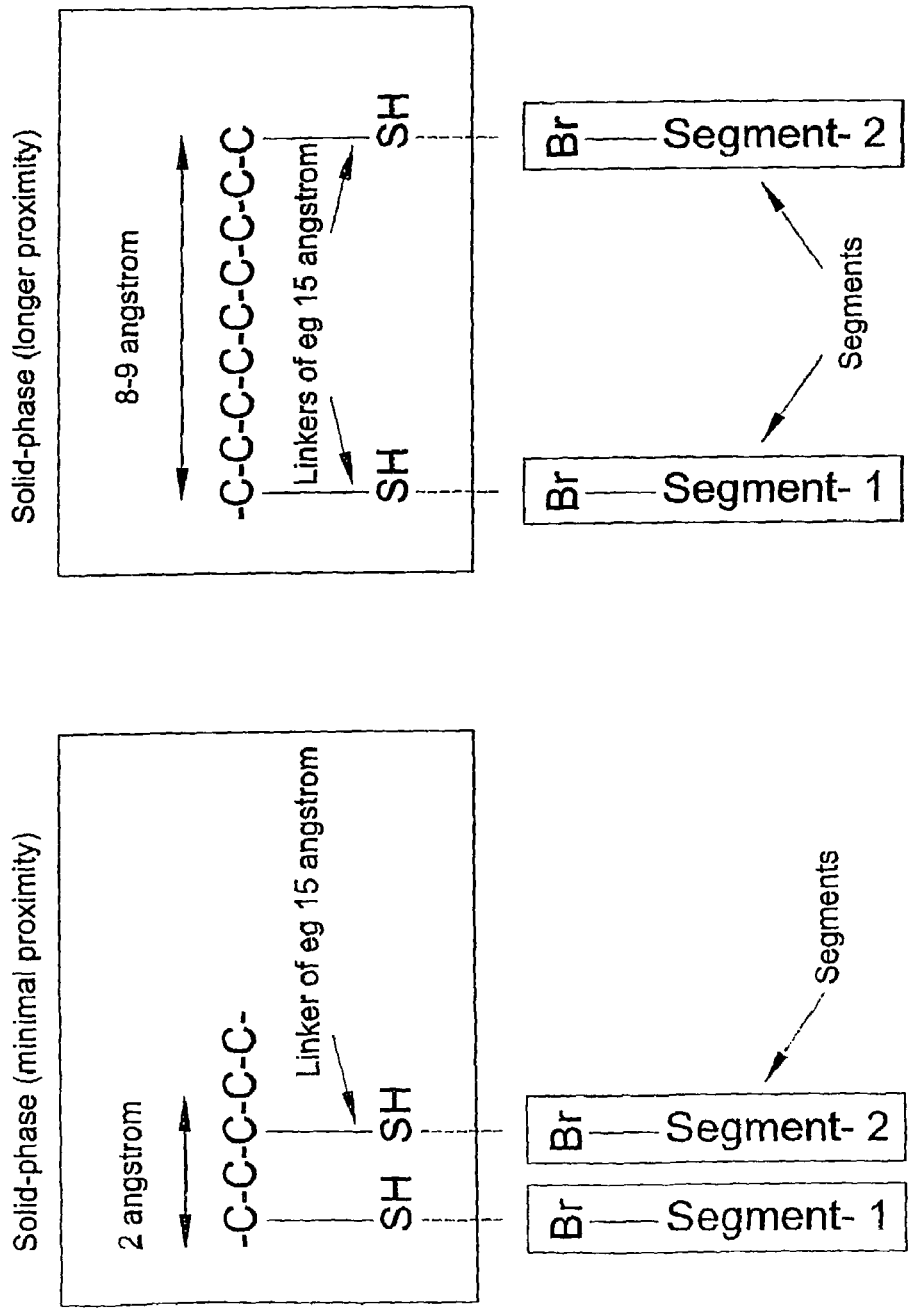
FIG. 3: Proximity of segments after coupling on solid-support. On the left side: on a minimal distance of 2 angstrom, linkers of 15 angstrom are coupled. The segments are coupled to these linkers. The flexibility of the linkers allows the termini of the two segments to move within distances of 0 to 30 angstroms. On the right side: the distances between the linkers can be varied from 2 to 50 or more. As an example, 9 angstrom is shown. This allows the termini of the two segments to move within distances of 0 to 40 angstroms.
Figure 10:
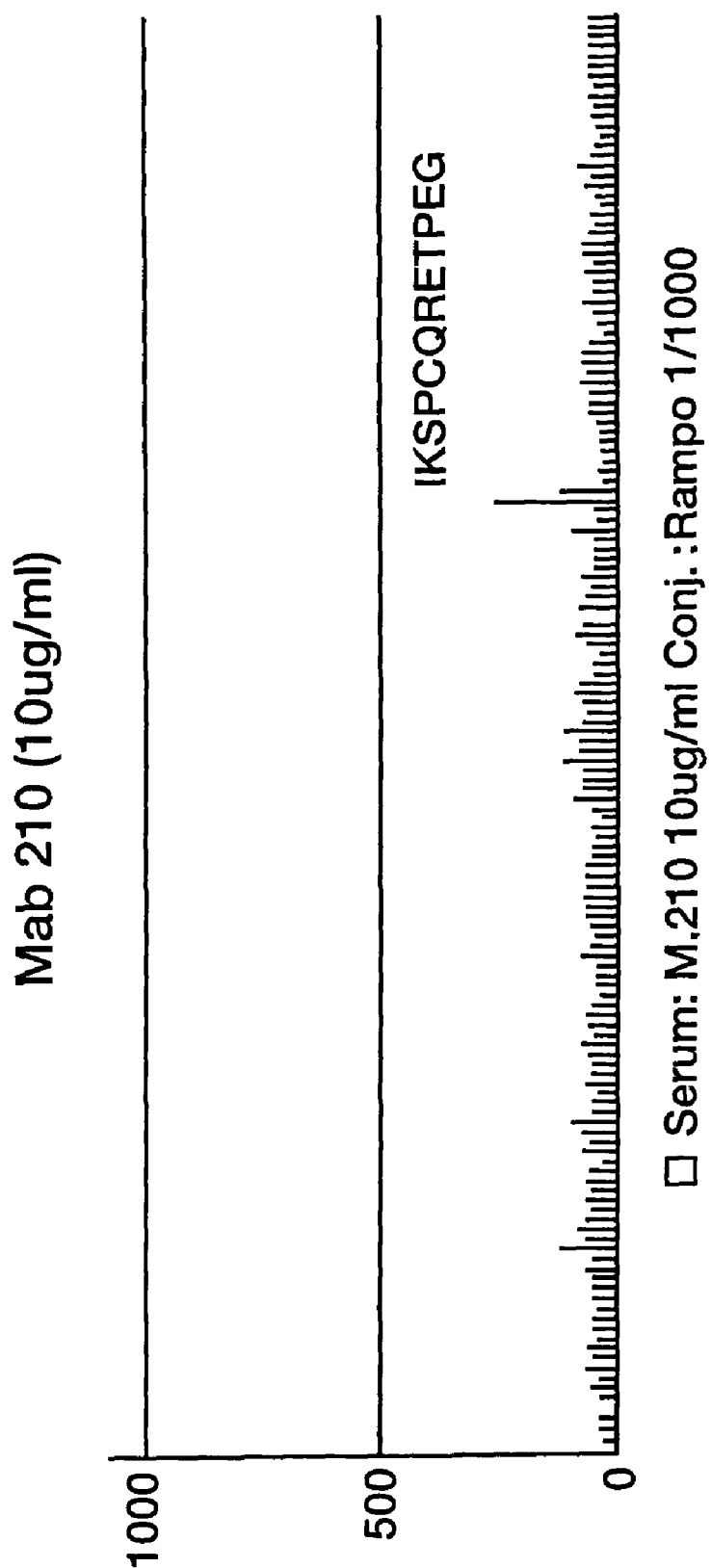
FIG. 10: Standard linear Pepscan on all overlapping synthetic 12-mers covering the linear sequence of hTNF with monoclonal antibody 210 (R&D Systems, MAB210, clone 1825.12, through ITK Diagnostics Uithoorn, The Netherlands). A small peak with the sequence IKSPCQRETPEG (SEQ ID NO: 2) was identified. The y-axis are optical density values (OD) obtained using a ccd-camera system. Rampo, rabbit-anti-mouse peroxidase (DAKO).
Figure 13:
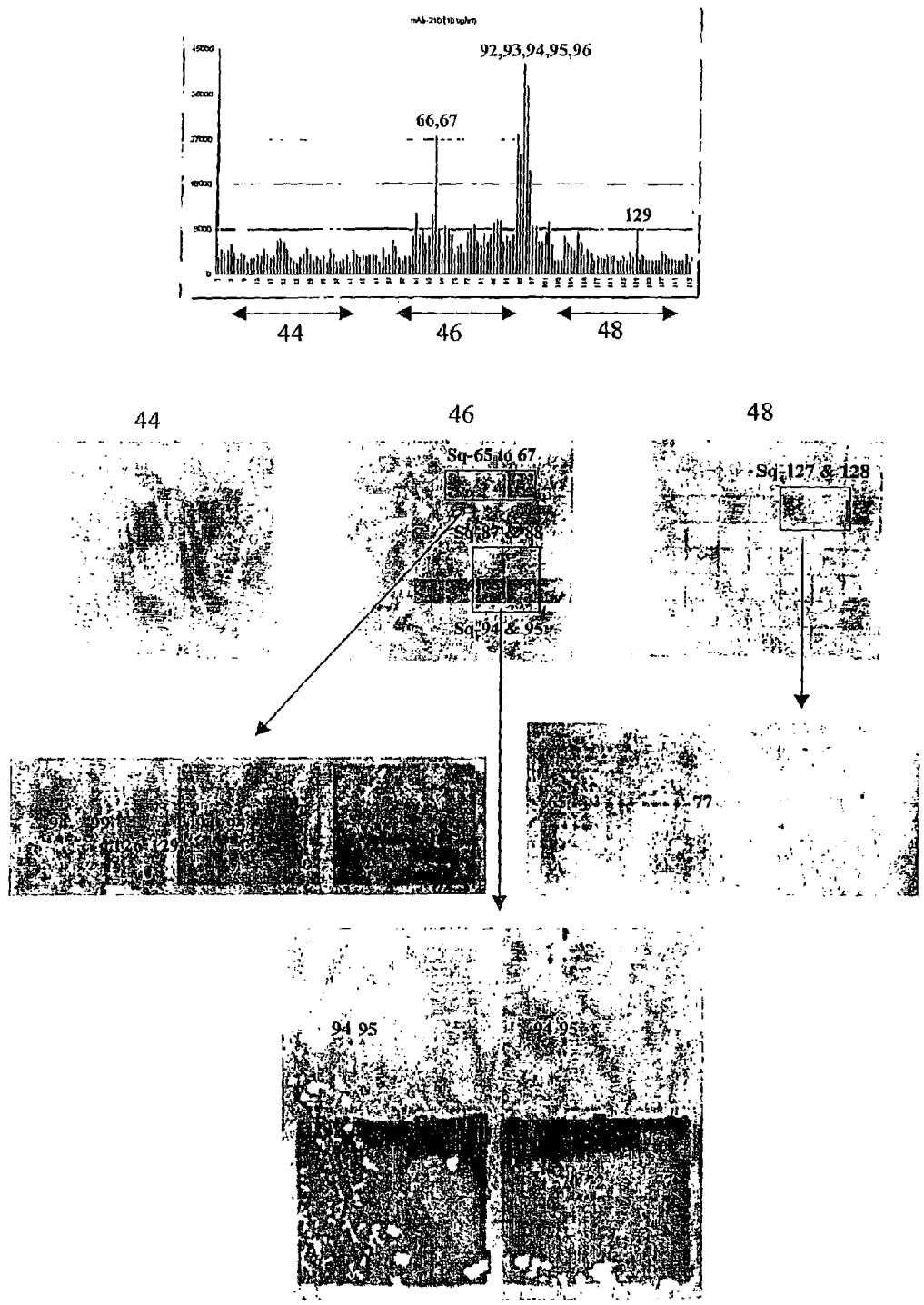
FIG. 13: Result of the loop-loop 15-mer Matrix-scan with anti-hTNF mAb 210 (10 ug/ml). The result obtained with all 145 squares is plotted. Squares 66, 67 and 92 to 96 are clearly labeled (firstly coupled loop-peptides). On top of these and other squares spots are labeled as well (spots represent first peptide coupled next to second loop peptide). Identified squares and spots: Sq-65:+FKGQGCPSTHVLLTZ (SEQ ID NO: 9); Sq-66:+KGQGCPSTHVLLTHZ (SEQ ID NO: 10); Sq-67:+GQGCPSTHVLLTHTZ (SEQ ID NO: 11); Sq-87:+SYQTKVNLLSAIKSZ (SEQ ID NO: 12); Sq-88:+YQT-KVNLLSAIKSPZ (SEQ ID NO: 13); Sq-94:+LLSAIKSPC-QRETPZ (SEQ ID NO: 14); Sq-95:+LSAIKSPCQRETPEZ (SEQ ID NO: 15); Sq-127:+LEKGDRLSAEINRPZ (SEQ ID NO: 16); Sq-128:+EKGDRLSAEINRPDZ (SEQ ID NO: 17); Peptide-65:+FKGQGCPSTHVLLTZ (SEQ ID NO: 18); Peptide-70:+CPSTHVLLTHTISRZ (SEQ ID NO: 19); Peptide-72:+STHVLLTHTISRIAZ (SEQ ID NO: 20); Peptide-77:+LTHTISRIAVSYQTZ (SEQ ID NO: 21); Peptide-94:+LLSAIKSPCQRETPZ (SEQ ID NO: 22); Peptide-95:+LSAIKSPCQRETPEZ (SEQ ID NO: 23); Peptide-99:+KSPCQRETPEGAEAZ (SEQ ID NO: 24); Peptide-126:+QLEKGDRLSAEINRZ (SEQ ID NO: 25); Peptide-129:+KGDRLSAEINRPDYZ (SEQ ID NO: 26). The y-axis is in arbitrary units.
Figure 15:
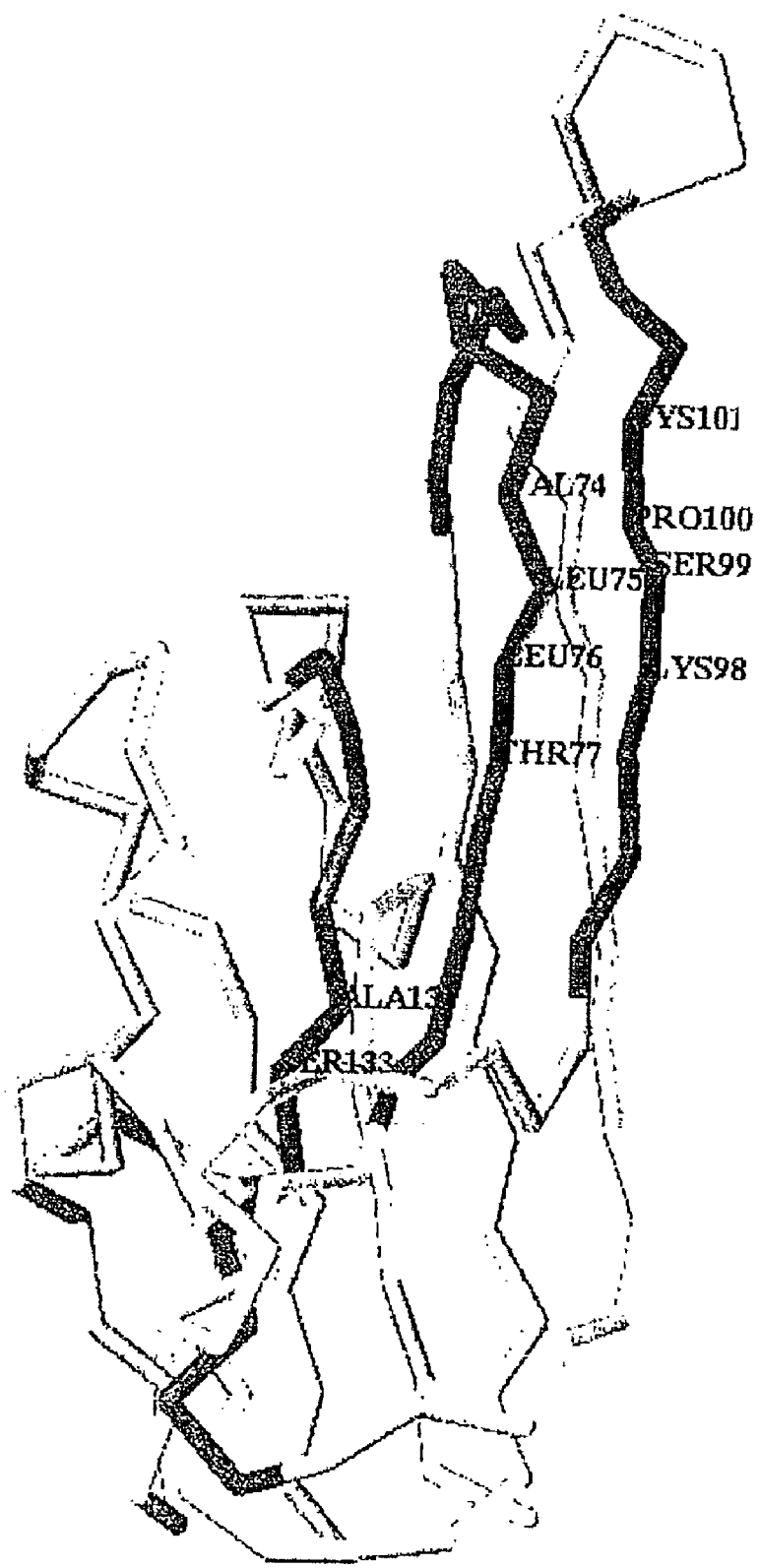
FIG. 15: Three dimensional representation of the identified binding loop-loop peptides with mAB-210 (10 ug/ml). Shown are the three regions identified (peptides 65-69, 94-96 and 1-26-127): GQGCPSTHVLLTHTIS (SEQ ID NO: 27) (VLLT are labeled); SAIKSPCQRE (SEQ ID NO: 28) (KSPC are labeled); KGDRLSAEINR (SEQ ID NO: 29) (SA are labeled).

The monoclonal antibody mAb-210 raised against hTNF was tested on linear and loop peptides (mAb-210 was bought from R&D Systems, MAB21O, clone 1825.12, through ITK Diagnostics Uithoorn, The Netherlands). Firstly, it was tested in Pepscan on all overlapping linear 12-mers covering hTNF. This resulted in a, minor peak around sequence IKSPC-QRETPEG (SEQ ID NO: 2) (FIG. 10). Secondly, it was tested in Pepscan matrix-scan on double 15-mer loop-loop peptides (as described in FIGS. 3 and 4 and explained through FIGS. 11-12). Two loop-regions were labeled: peptide sequence GQGCPSTHVLLT (SEQ ID NO: 65) (squares 65 to 67) and SAIKSPCQRE (SEQ ID NO: 28) (squares 92 to 96) (FIGS. 13, 14). In addition in various squares loop peptide spots were identified corresponding to sequence GQGCPSTHVLLT (SEQ ID NO: 65) (spots 65-67); SAIKSPCQRE (SEQ ID NO: 28) (spots 92-96) and KGDRLSAEINR (SEQ ID NO: 29) (spots 126-129) (FIG. 14). These three regions, illustrated in FIG. 15 on the three-dimensional model of hTNF, are located on one side of the hTNF molecule and form one large discontinuous epitope region.

Figure 16:
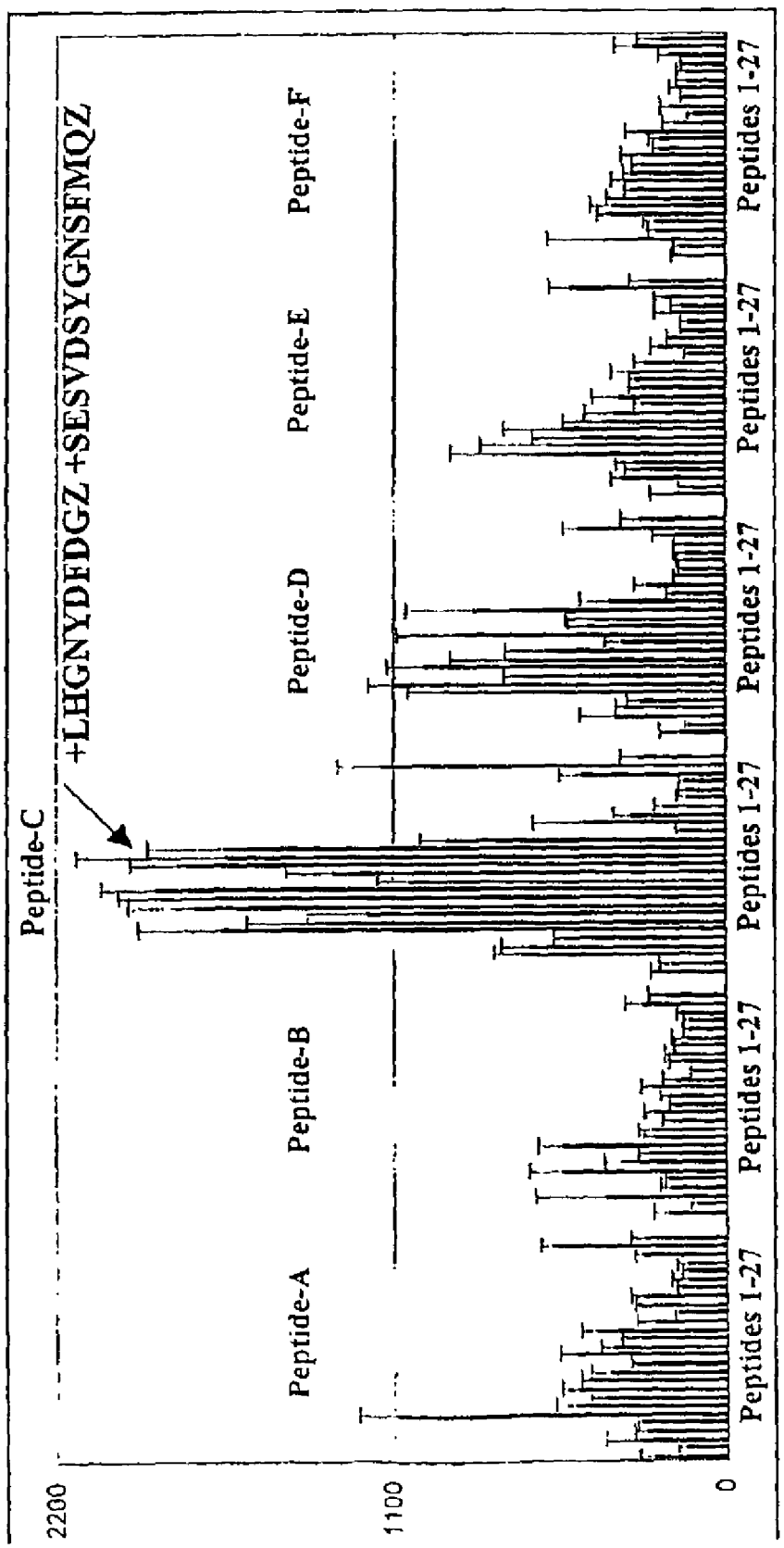
FIG. 16: Result of the loop-loop 15-mer Matrix-scan of loop-loop CDR-regions of antibodies with lysozyme-biotin (100 ug/ml, in triplo). Using 1 µg/ml lysozyme-biotin no binding is observed (not shown). Controls of only streptavidin-peroxidase in between the tests were negative (not shown). Peptides A, B, C, D, E and F: Peptide-A.

Identification of Synthetic Mimics of Antibodies (Binding Bodies) (FIG. 16).

From six different antibodies, the HCDR3-region (complementary determining region three of the antibody heavy chain) was synthesized as synthetic loop-peptides. As an example, four different anti-lysozyme antibodies and two different anti-choriogonadotrophin antibodies were selected: 1fdl.pdb (D1.3), 1 mlb.pdb (D44.1), 3hfl.pdb (HyHel-5), 3hfm.pdb (HyHel-10) all anti-lysozyme, and 1qfw.pdb, two anti-human choriogonadotrophin, one anti-alpha and one anti-beta. The synthetic loop peptides were coupled to the minicards as described above. The three-dimensional coordinates (pdb-files) were extracted from the Protein Data Bank (PDB) at www.rcsb.org (RCSB, Research Collaboratory for Structural Bioinformatics) (Berman et al., 2000, The Protein Data Bank. Nucleic Acids Research, 28 pp. 235-242; Bernstein et al. 1977, The protein data bank: A computer-based archival file for macromolecular structures. J. Mol. Biol. 112 :535-542).

Figure 3B:
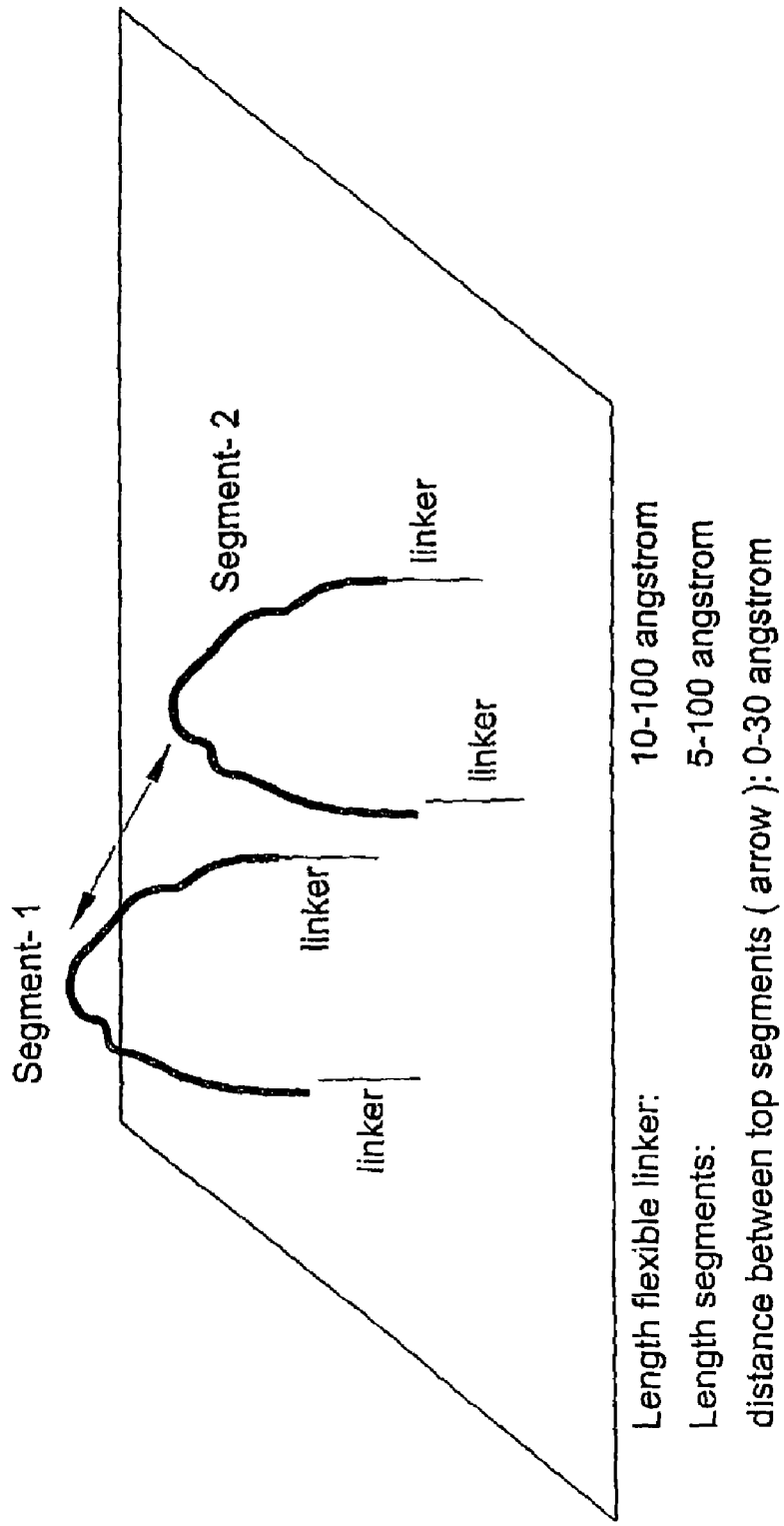
FIG. 3B: Schematic representation of how the two segments are linked as loops to the poly-carbon polymer surface. The preferred distances, at least in the case of CDR-derived binding bodies, between the tops of the loops are 0 to 30 angstroms, which is similar to that of the CDRs in an antibody.

Together with each of the six peptides, 27 different other loop peptides were coupled to the minicard as described in FIG. 3B: thus, group-1 was a loop of HCDR3 of 1fdl.pdb coupled next to 27 different loops covering LCDR1, LCDR2 or LCDR3, group-2 was a loop of 1mlb.pdb coupled next to 27 different loops covering LCDR1, LCDR2 or LCDR3, etc. (LCDR, complementary determining region three of the antibody light chain). The 27 different loop peptides represented LCDR1, LCDR2 or LCDR3 of the same antibodies described above (1 fdl.pdb, 1 mlb.pdb, 3hfl.pdb, 3hfm.pdb or 1qfw.pdb).

The result is shown in FIG. 16 (6 groups with 27 loop-loop coupled peptides). The six loop-loop coupled peptides with the highest binding activity were: +LHGNYDFDGZ (SEQ ID NO: 32) +SESVDSYGNSFMQZ (SEQ ID NO: 46) (loop of HCDR3 of 3hfl.pdb and loop of LCDR1 1qfw.pdb, respectively) (see FIG. 16); +LHGNYDFDGZ (SEQ ID NO: 32) +RASESVDSYGNSFMQZ (SEQ ID NO: 49) (loop of HCDR3 of 3hfl.pdb and loop of LCDR1 1qfw.pdb, respectively); +LHGNYDFDGZ (SEQ ID NO: 32) +RASES-VDSYGNSFZ (SEQ ID NO: 44) (loop of HCDR3 of 3hfl.pdb and loop of LCDR1 1qfw.pdb, respectively); +LHGNYD-FDGZ (SEQ ID NO: 32) +ASESVDSYGNSFMZ (SEQ ID NO: 45) (loop of HCDR3 of 3hfl.pdb and loop of LCDR1 1qfw.pdb, respectively); +LHGNYDFDGZ,(SEQ ID NO: 32) +ASESVDSYGNSFZ (SEQ ID NO: 41) (loop of HCDR3 of 3hfl.pdb and loop of LCDR1 1qfw.pdb, respectively); +LHGNYDFDGZ (SEQ ID NO: 32) +LLVYYTTTLADGZ (SEQ ID NO: 51) (loop of HCDR3 of 3hfl.pdb and loop of LCDR2 1fdl.pdb, respectively).

The loop-loop peptide pair, +LHGNYDFDGZ (SEQ ID NO: 32) +SESVDSYGNSFMQZ (SEQ ID NO: 46) (loop of HCDR3 of 3hfl.pdb with loop of LCDR1 of 1qfw.pdb, respectively) that has the highest binding activity is indicated by an arrow (FIG. 16). This loop-loop peptide pair is derived from an anti-lysozyme antibody and an anti-human choriogonadotrophin antibody. The results shown in FIG. 16 shows that particular pairs of synthetic CDRs show better binding to lysozyme than other pairs, especially group-C. Therefore, loop-loop combinations of synthetic loops representing different CDRs of (different) antibodies, not necessarily derived from the original antibody which in this example is an anti-lysozyme antibody, can be used to identify lead synthetic compounds that mimic antibodies.

Construction of a Double-Loop Mimic of a Discontinuous Epitope (FIG. 17).

Figure 4:
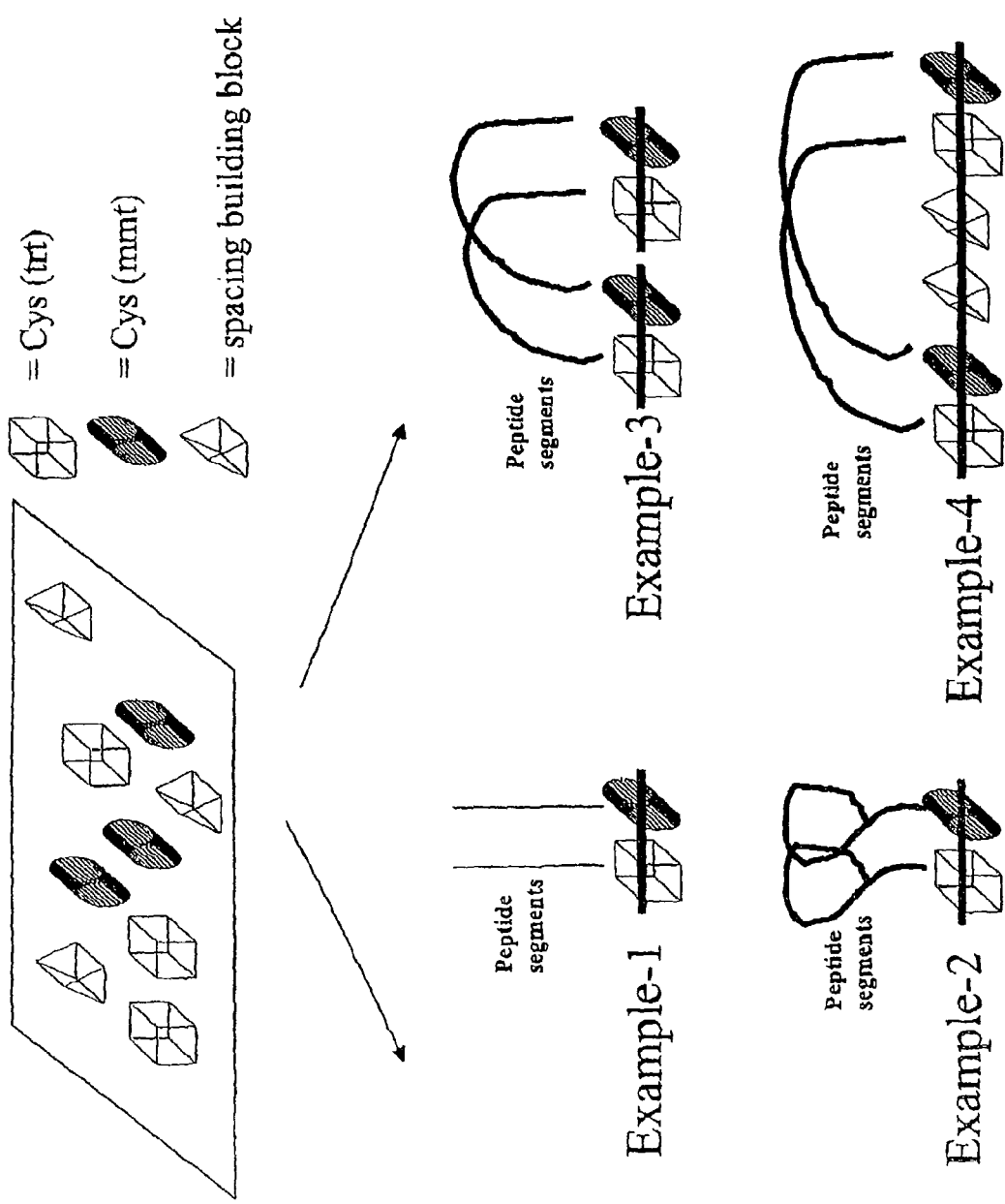
FIG. 4: Schematic representation of how two segments can be coupled onto the (polycarbon)-polymer surface. The drawing shows four examples. In Example-1, two linear segments are coupled. In Example-2, two looped segments are coupled. In Example-3, two segments are coupled as loops. In Example-4, two segments are coupled as loops. With extra spaced building blocks (e.g., phenylalanine amino acids) two obtain extended loops. On the (polyearbon)-surface, two types of protected cysteines (cys (trt) and cys (mmt) ) and, for example, one spacing building block is coupled. The cys (mmt) is deprotected with 1% TFA, while the cys (trt) remains protected. The first segment is coupled to the deprotected cys (mmt). Then, the second cys (trt) is deprotected with 95% TFA. Then, the second segment is coupled to the now deprotected cys (trt).
Figure 4B:
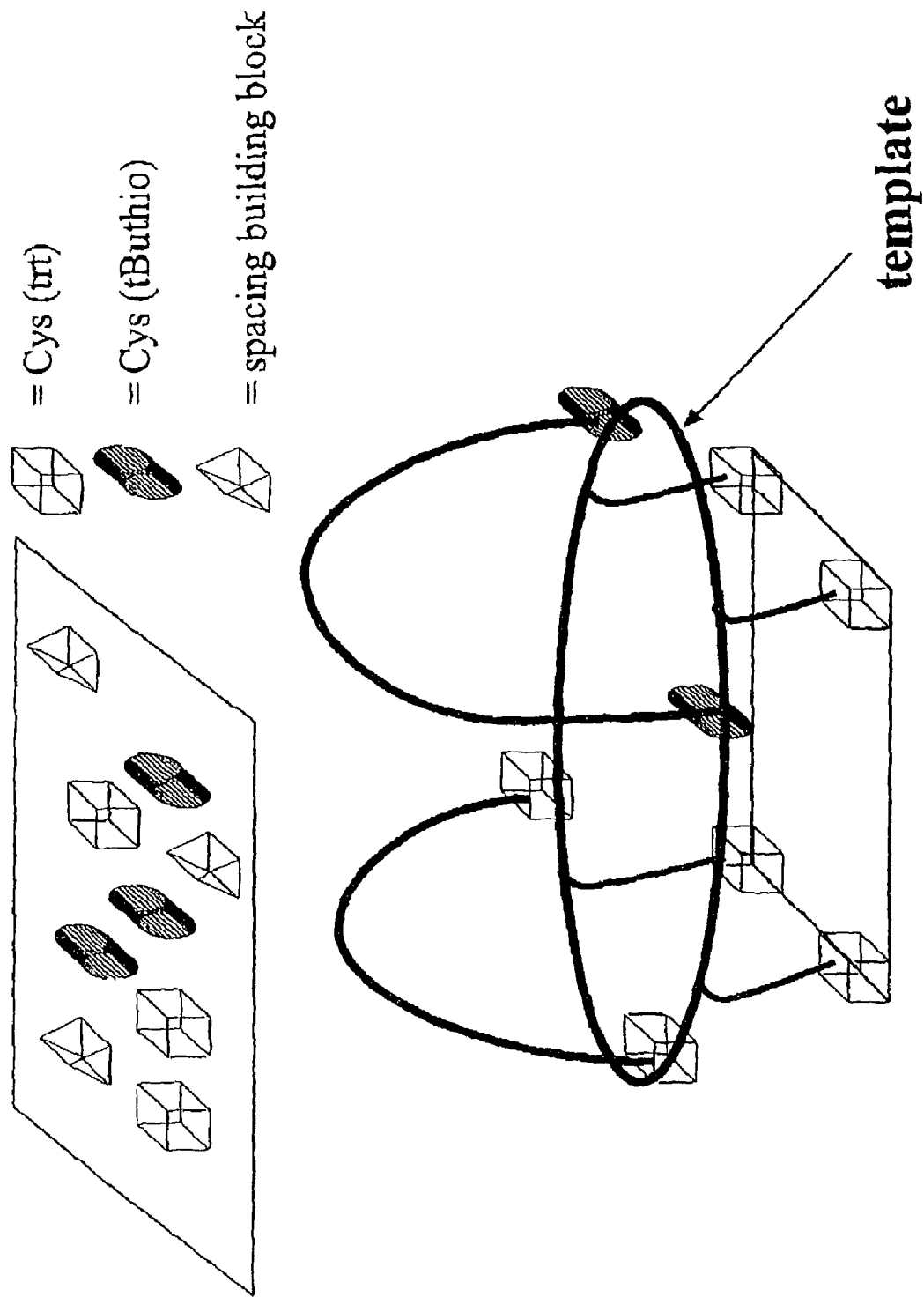
FIG. 4B: Schematic representation of how two segments can be coupled onto a cyclic template that itself is coupled to the polymer surface. The cyclic template is a cyclic flexible peptide. The cyclic peptide contains four lysines (mmt), two cysteines (trt) and two cysteines (butyl). The peptide is coupled to the resin via a sulphur that is sensitive to 1% TFA. At the amino-terminus, a bromine is attached as described previously. The procedure is as follows: The synthesized peptide is treated with 1% TFA. This results in deprotection of the lysines and de-coupling of the peptide from the resin. The cysteines remain protected. After raising the pH to 8, the N— and C-terminus of the peptide are linked through the S and Br. Then, the —$NH_2$ on the deprotected lysines is coupled to Br. The resulting cyclic peptide, with four Br and still four protected cysteines, is coupled to the linkers via the Br. To the cyclic template coupled to the linker-cysteines, two peptide segments are coupled. First, the two cysteines (trt) are deprotected with 95% TFA. Then, the first segment is coupled. Second, the two cys (butyl) are deprotected with $NaBH_4$. Then, the second segment is coupled.
Figure 4C:
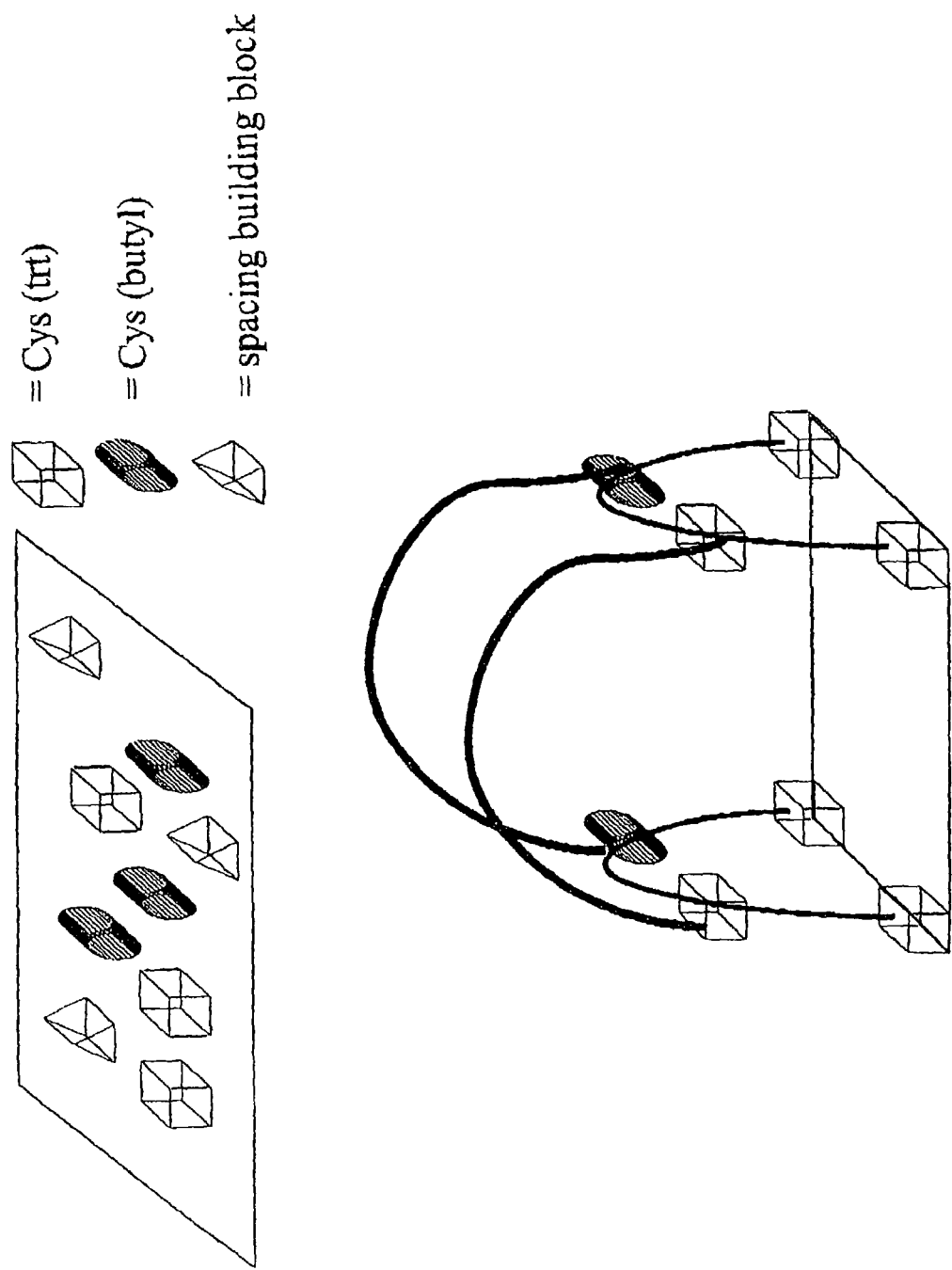
FIG. 4C: Schematic representation of how two segments can be coupled onto two other segments that are coupled to the polymer surface. With free —SH on the surface, two segments are coupled to the surface via a N— and C-terminal Br. The N-terminal Br is synthesized as described previously. The C-terminal Br is linked to a C-terminal Lysine as described in FIG. 4B. Both segments contain protected cysteines on which two other segments are also coupled, as described in FIG. 4B.
Figure 5:
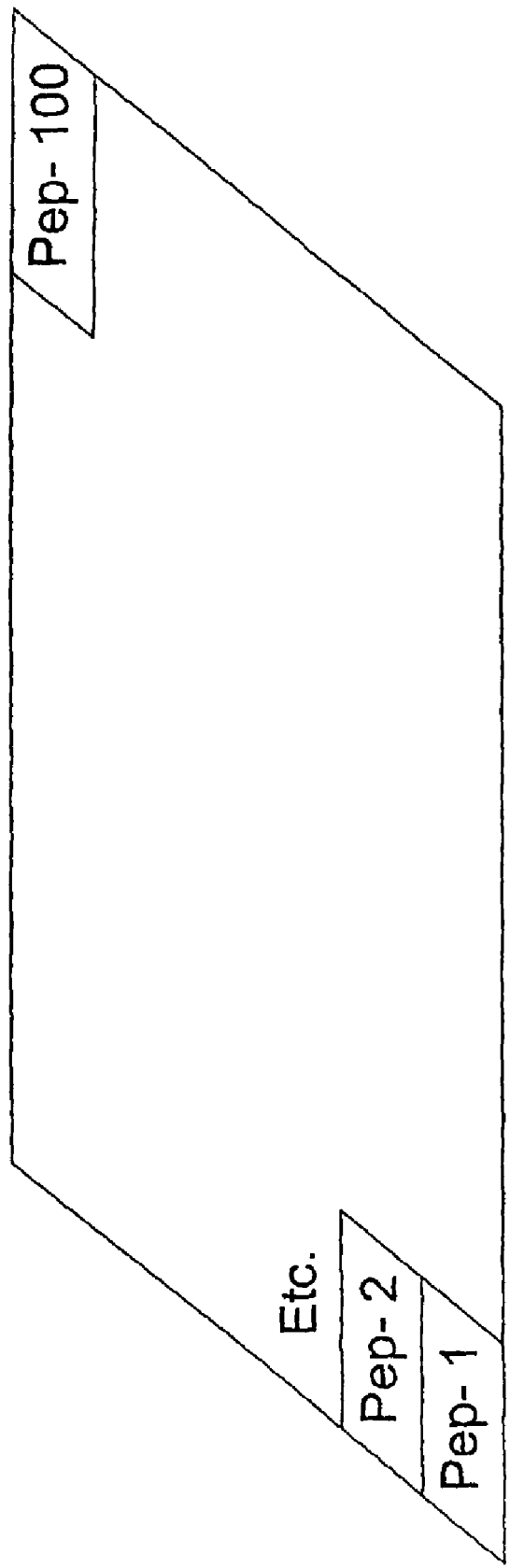
FIG. 5: Schematic representation of matrix-scan with two segments. On the polymer surface, a mixture of cys (mmt) and cys (trt) are coupled. After 1% TFA, the cys (mmt) is deprotected. Then, in each square one peptide is coupled via one or two terminal Br. Thus, peptide-1 in square-1, peptide-2 in square-2, etc., to peptide-100 in square-100. Then, the cys(trt) is deprotected with 95% TFA. Then, 100 different peptides are spotted in each square. Thus, peptide-1 to 100 in square-1, peptide 1 to 100 in square-2, etc., to peptide-1 to peptide-100 in square-100.
Figure 6:
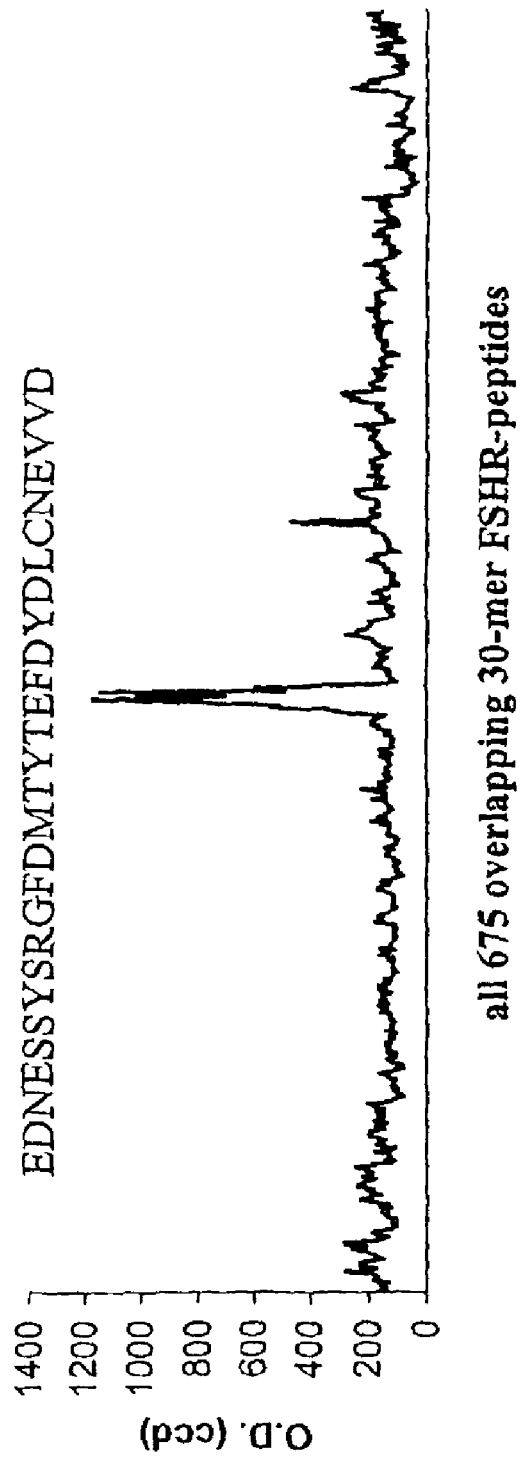
FIG. 6: Binding-assay of all overlapping 30-mers covering the linear sequence of hFSHR with the biotinylated synthetic 40-mer hFSH-peptide biotin-EKEEARFCIS-INTTWAAGYAYTRDLVYKDPARPKIQKTAT-CONH2 (SEQ ID NO: 1). The 30-mer peptides were spotted as described, and the 40-mer peptides were synthesized using standard FMOC-chemistry. The various 30-mer peptides were incubated with 1 microgram/ml hFSH-peptide. After washing, the peptides were incubated with streptavidin-peroxidase, and subsequently after washing, with peroxidase substrate and $H_2O_2$.
Figure 7:
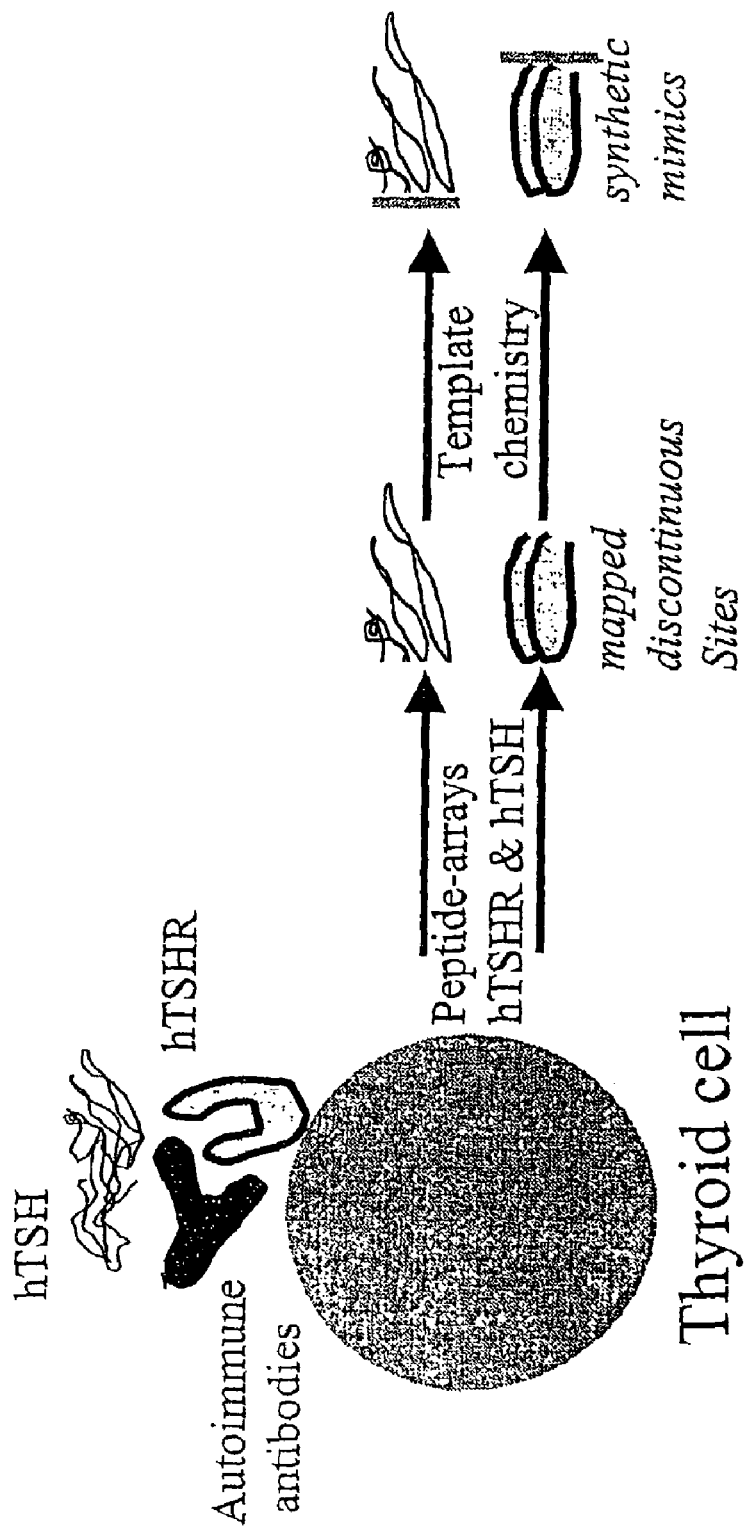
FIG. 7: Schematic representation of the development of synthetic mimics of discontinuous binding sites on the hTSHR and hTSH. On thyroid cells, the hTSH-receptor binds hTSH. The autoimmune antibodies from Graves and Hashimoto patients also bind the hTSH-receptor. Through screening of all overlapping 30-mers of hTSH, segments of the discontinuous binding site for hTSHR are identified (as described for FSH, see legend FIG. 6). Through screening of all overlapping 30-mers of hTSHR, segments of the discontinuous binding sites for Graves and Hashimoto antibodies are identified. Through modeling and usage of synthetic templates, the individual segments are combined into one discontinuous synthetic mimic.
Figure 8:
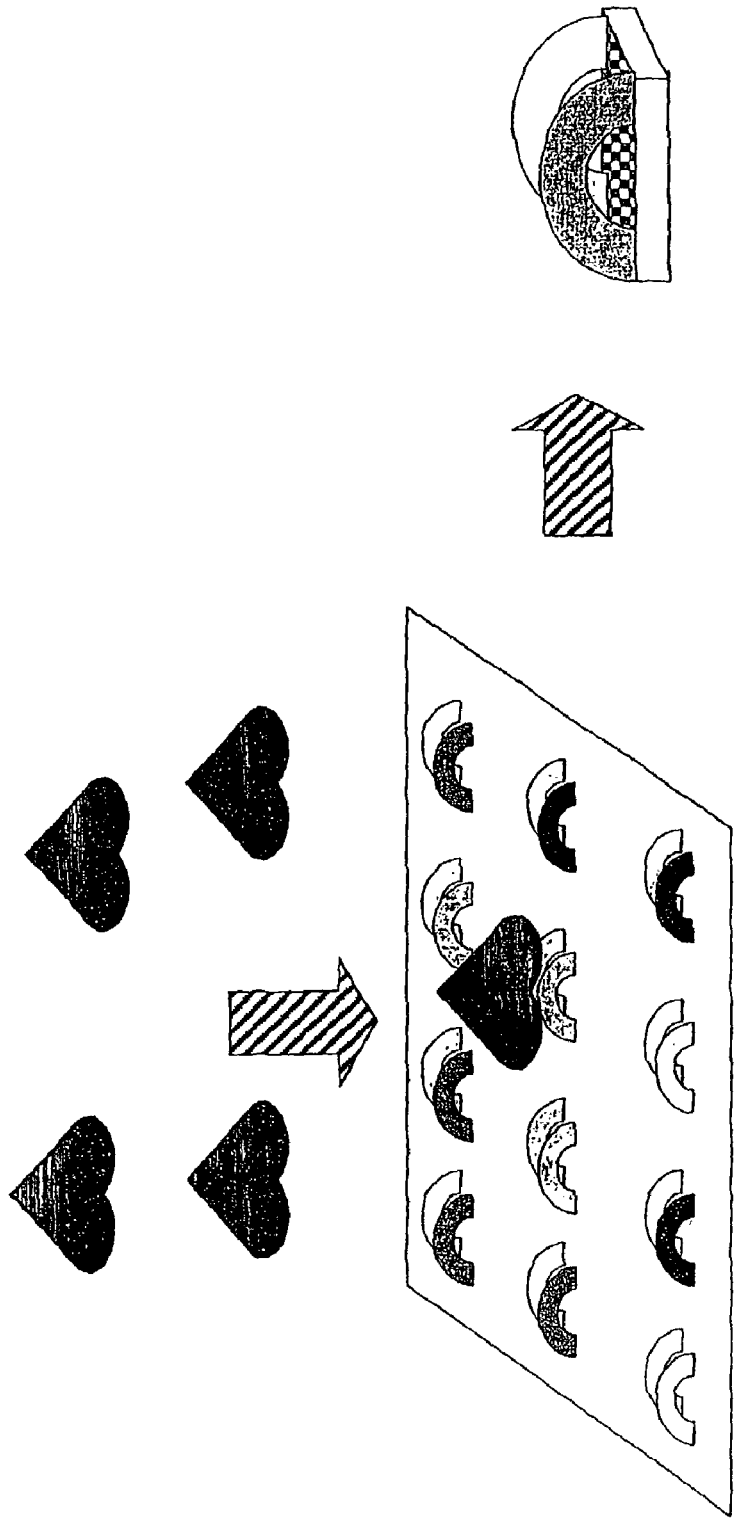
FIG. 8: Schematic representation of an array comprising synthetic mimics of discontinuous binding sites or binding bodies. Binding bodies are selected and improved by making arrays that contain a multiplicity of spatially addressable binding bodies on the solid surface (or, alternatively, on a separate molecular scaffold). The arrays can be incubated with target to screen for binding bodies that bind the target of interest. Lead binding bodies can be improved by making follow-up arrays composed of multiple variants of the lead binding bodies, e.g., by sequence shuffling. If the desired specificity and/or affinity is reached, the binding bodies can be produced onto a scaffold and produced and used in bulk.
Figure 9:
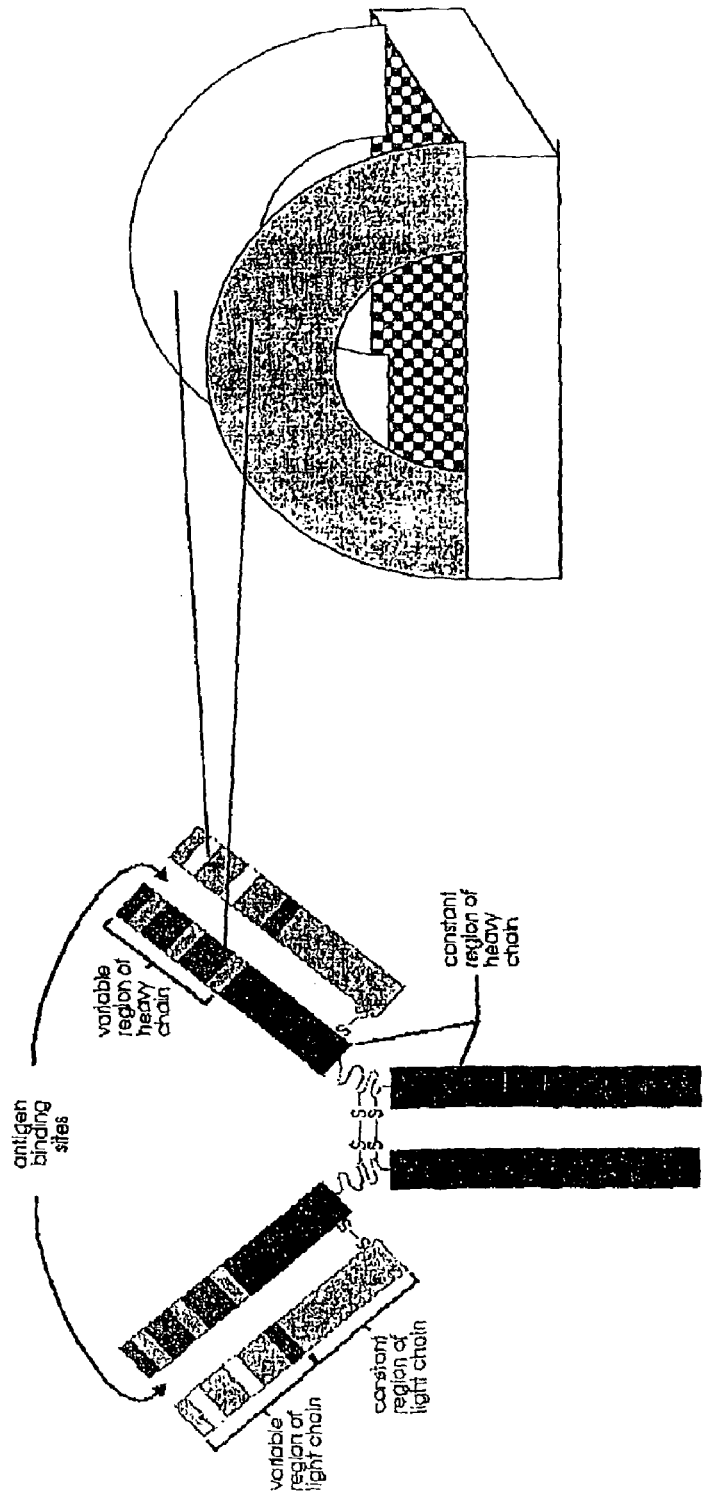
FIG. 9: Schematic representation of the development of synthetic mimics of discontinuous binding sites or binding bodies derived from CDR sequences. Binding bodies are constructed by positioning on a solid phase or array surface (preferably a (polycarbon)-polymer surface) or on predefined scaffolds or templates. Binding bodies can be derived from the Complementarity Determining Regions (CDRs) of antibodies or any other protein motif that is known to bind other molecules, preferably with high affinity.

Two peptides that constitute two separate parts of a discontinuous epitope were coupled to the surface of a minicard as described above in the legend of FIG. 12 (cf FIG. 3A and FIG. 4 (example-4)). A cys(mmt) was coupled alone or in combination with a cys(trt) (in a 1:1 ratio) and/or val(mmt) (the cys and val in a 1:1, 1:3, 1:9 etc. ratio). In this way one peptide was coupled (squares A and C) or two peptides with increasing valines in between the cysteines were coupled (squares B and D) (cf FIG. 4B (example-4), FIG. 17). These four configurations were incubated with two different antibodies.

Antibody-1 recognized, when the individual loop peptides are coupled as a single loop, only loop peptide-2. Antibody-2 recognized, when the individual loop peptides are coupled as a single loops, only loop peptide-1. When the two loop peptides are combined, antibody-1 showed a higher binding activity with peptide-1 as coupled first. When the two loop peptides are combined, antibody-2 showed not a higher binding activity.

The results shown in FIG. 17 show that particular pairs of synthetic loops of a discontinuous epitope show improved binding to a particular antibody. Therefore, combinations of synthetic loops that are part of a discontinuous epitope can be used to identify lead synthetic compounds that mimic discontinuous epitopes.

What is claimed is:

1. A method for producing a molecular library for identification or detection of a binding site of a molecule, the method comprising:
   providing a plurality of test entities wherein each test entity comprises a first peptide and a second peptide;
   positioning the first peptide on a solid phase; and
   positioning the second peptide on the solid phase;
   wherein said first peptide and said second peptide are distinct and located no more than 100 Angstrom (Å) apart from one another and wherein the first and second peptides are linked at each end thereof to the solid phase, thereby forming looped peptides.

2. The method according to claim 1, wherein said solid phase comprises an array surface.

3. The method according to claim 1, wherein at least said first peptide is linked by a thioether bond to said solid phase.

4. The method according to claim 1, wherein said first peptide is no more than 50 Å apart from the second peptide.

5. The method according to claim 1, wherein said first peptide is no more than 30 Å apart from the second peptide.

6. The method according to claim 1, wherein said first peptide is no more than 15 Å apart from the second peptide.

7. The method of claim 1, wherein the first peptide and second peptide are random peptides.

8. A method for producing a molecular library for identification or detection of a binding site of a molecule, the method comprising:
providing a plurality of test entities wherein each test entity comprises a first peptide and a second peptide;
positioning the first peptide on a solid phase; and
positioning the second peptide on the solid phase;
wherein the first peptide and the second peptide are distinct, wherein the first peptide and the second peptide are selected at random, wherein the first peptide and second peptide are located no more than 100 Angstrom (Å) apart from one another, and wherein the first and second peptides are linked at each end thereof to the solid phase, thereby forming looped peptides with said first and second peptides.

9. A method for producing a molecular library for identification or detection of a binding site of a molecule, the method comprising:
providing a plurality of test entities wherein each test entity comprises a first peptide and a second peptide;
positioning the first peptide on a solid phase; and
positioning the second peptide on the solid phase;
wherein the first peptide and the second peptide are distinct, and wherein the first peptide and second peptide are located no more than 100 Angstrom (Å) apart from one another and wherein the first and second peptides are linked at each end thereof to the solid phase, thereby forming looped peptides with respect to the solid phase.

10. A method of producing a molecular library, the method consisting of:
producing a plurality of test entities, each said test entity comprising a first random peptide and a respective, different second random peptide, and
immobilizing said plurality test entities onto a solid phase so that, after immobilization, each first random peptide is positioned onto the solid phase no more than 100 Angstrom (Å) apart from the respective second random peptide thereof and wherein the first and second peptides are linked at each end thereof to the solid phase, thereby forming looped peptides,
so as to produce said molecular library.

11. A method of producing a molecular library for identifying or detecting a binding site of a ligand of a binding molecule, the method comprising:
providing a plurality of test entities, each said test entity comprising a first peptide and a respective, different second peptide, and
immobilizing said plurality of test entities onto a solid phase so that, after immobilization, each first peptide is positioned onto the solid phase no more than 100 Angstrom (Å) apart from the respective second peptide thereof, wherein the first and second peptides are linked at each end thereof to the solid phase, thereby forming looped peptides,
so as to produce said molecular library.

12. The method according to claim 9, wherein each of at least the first peptide and/or the second peptide represents a potential part of a discontinuous binding site.

* * * * *

UNITED STATES PATENT AND TRADEMARK OFFICE
CERTIFICATE OF CORRECTION

PATENT NO. : 7,972,993 B2  Page 1 of 1
APPLICATION NO. : 10/411869
DATED : July 5, 2011
INVENTOR(S) : Jelle Wouter Slootstra et al.

It is certified that error appears in the above-identified patent and that said Letters Patent is hereby corrected as shown below:

On the title page:
In Item (56) References Cited
FOREIGN PATENT DOCUMENTS
Page 1, 2$^{nd}$ column, 3rd entry,    change "WO 98/09411" to --WO 96/09411--

Signed and Sealed this
Fifth Day of February, 2013

Teresa Stanek Rea
*Acting Director of the United States Patent and Trademark Office*